US009340795B2

(12) United States Patent
Kisaka et al.

(10) Patent No.: US 9,340,795 B2

(45) Date of Patent: May 17, 2016

(54) GENETICALLY MODIFIED PLANT CAPABLE OF BIOSYNTHESIZING CAPSINOID

(75) Inventors: Hiroaki Kisaka, Kawasaki (JP); Yaqin Lang, Kawasaki (JP); Ryuji Sugiyama, Kawasaki (JP); Tetsuya Miwa, Kawasaki (JP); Susumu Yazawa, Kameoka (JP)

(73) Assignee: AJINOMOTO CO., INC., Tokyo (JP)

( * ) Notice: Subject to any disclaimer, the term of this patent is extended or adjusted under 35 U.S.C. 154(b) by 504 days.

(21) Appl. No.: 12/976,526

(22) Filed: Dec. 22, 2010

(65) Prior Publication Data

US 2011/0166371 A1 Jul. 7, 2011

Related U.S. Application Data

(63) Continuation-in-part of application No. PCT/JP2009/061169, filed on Jun. 19, 2009.

(30) Foreign Application Priority Data

Jun. 23, 2008 (JP) ................................ 2008-163884

(51) Int. Cl.

*C12N 15/82* (2006.01)
*C12N 15/87* (2006.01)
*C12P 7/62* (2006.01)
*C12P 13/02* (2006.01)

(52) U.S. Cl.

CPC ........ *C12N 15/8243* (2013.01); *C12N 15/8218* (2013.01); *C12N 15/8285* (2013.01); *C12P 7/62* (2013.01); *C12P 13/02* (2013.01)

(58) Field of Classification Search

CPC ........... C12N 15/8243; C12N 15/8285; C12N 15/8218; C12P 7/62; C12P 13/02
USPC ................................................. 800/278, 285
See application file for complete search history.

(56) References Cited

U.S. PATENT DOCUMENTS 6,142,349 A * 11/2000 Roberson ...................... 224/401
6,723,897 B2 * 4/2004 Brown et al. ................. 800/290

OTHER PUBLICATIONS

Juarez et al., Virus-induced silencing of Comt, pAmt, and Kas genes results in a reduction of capsaicinoid accumulation in chili pepper fruits, 227 Planta, 681-695 (2008).*

Rapid Communications, Novel capsaicinoid-like substances, Capsiate and Dihydrocapsiate, from the Fruits of Nonpugent Cultivar, CH-19 Sweet, of Pepper (*Capsicum annuum* L.), 46 J of Agic & Food Chem No. 5, 1695-1697 (1998).*

International Preliminary Report on Patentability in International Application No. PCT/JP2009/061169.

Y. Tanaka, et al., "Novel Loss-Of-Function Putative Aminotransferase Alleles Cause Biosynthesis of Capsinoids, Nonpungent Capsaicinoid Analogues, in Mildly Pungent chili Peppers (*Capsicum chinese*)", J. Argic. Food Chem., 2010, vol. 58, pp. 11762-11767.

R. Abraham-Juarez, et al., "Virus-Induced Silencing of Comt, pAmt and Kas Genese Results in a Reduction of Capsaicinoid Accumulation in Chili Pepper Fruits", Planta, 2008, vol. 227, pp. 681-695.

Rapid Communications, "Novel Capsaicinoid-like Substances, Capsiate and dihydrocapsiate, From the Fruits of a Nonpungent Cultivar, CH-19 Sweet, of Pepper (*Capsicum annuum* L.)", J. Agric. Food Chem., vol. 46, No. 5, May 1998, pp. 1695-1697.

K. Sutoh, et al., "Capsinoid Is Biosynthesized from Phenylalanine and Valine in Non-Pungent Pepper, *Capsicum annuum* L. ev. CH-19 Sweet", Biosci. Biotechnol. Biochem., vol. 60, No. 6, 2006, pp. 1513-1516.

V. Lang, et al., "Functional loss of pAMT results in biosynthesis of capsinoids, capsaicinoid analogs, in *Capsicum annuum* cv. CH-19 Sweet", The Plant Journal, vol. 59, 2009, pp. 953-961.

E. Blum, et al., "Molecular mapping of capsaicinoid biosynthesis genes and quantitative trait loci analysis for capsaicinoid content in Capsicum", Theor. Appl. Genet., vol. 108, 2003, pp. 79-86.

Database DDBJ/EMBL/GenBank [online], Nov. 20, 1998, Accession No. AF085149.

D. Li, et al., "Establishment of a highly efficient transformation systems for pepper (*Capsicum annuum* L.)", Plant Cell Rep., vol. 21, 2003, pp. 785-788.

S. Oh, et al., "Capsicum annuum WRKY protein CaWRKY1 is a negative regulator of pathogen defense", New Phytologist, vol. 177, 2008, pp. 977-989.

* cited by examiner

*Primary Examiner* — Li Zheng

(74) *Attorney, Agent, or Firm* — Oblon, McClelland, Maier & Neustadt, L.L.P.

(57) ABSTRACT

The present invention provides a genetically modified plant that biosynthesizes an increased amount of capsinoids, a method of producing the genetically modified plant, and a production method of capsinoids from the genetically modified plant. More particularly, the present invention provides a genetically modified plant capable of producing capsinoids, which shows a decreased expression or activity of an enzyme that catalyzes an amino group conversion reaction from vanillin to vanillylamine as compared to wild strains, and the like. As a method of suppressing expression or activity of an enzyme, an introduction of DNA encoding an antisense RNA, iRNA, ribozyme or dominant-negative mutant for the target gene, a destruction of the gene by a knockout method, mutagen treatment or transposon insertion, an introduction of a gene encoding an antibody against the enzyme and the like can be mentioned.

12 Claims, 9 Drawing Sheets

(a)

(b)

GENETICALLY MODIFIED PLANT CAPABLE OF BIOSYNTHESIZING CAPSINOID

This application is a continuation-in-part of International Application PCT/JP2009/061169, filed on Jun. 19, 2009, claiming the foreign priority to JP 2008-163884, filed on Jun. 23, 2008. Both of these application are incorporated herein by reference in their entirety.

FIELD OF THE INVENTION

The present invention relates to a genetically modified plant that biosynthesizes an increased amount of capsinoids, a method of producing the genetically modified plant, a production method of capsinoids from the genetically modified plant and the like.

BACKGROUND OF THE INVENTION

Capsaicinoid compounds (capsaicin, dihydrocapsaicin etc.), which are a pungent component of chili pepper, are effective for preventing obesity, since these compounds promote energy metabolism, stimulate central nerves to promote hormone secretion and activate lipolytic enzyme. In addition, these compounds sterilize the gastrointestinal tract and improve immunity, and are also effective for activating immunity and relieving fatigue. However, since capsaicinoids irritate mucosa, ingestion in large amounts may upset the gastrointestinal tract. Moreover, individual people do not enjoy the pungent flavor and taste of capsaicinoid compounds.

As less pungent chili pepper, "CH-19 Sweet" (Variety Registration No. 10375), which is a nonpungent fixed variety of chili pepper selected and fixed by Yazawa et al. has been reported to contain a large amount of novel capsinoids (e.g., non-patent document 1). Such compounds belonging to capsinoids (fatty acid ester of vanillyl alcohol, capsiate, dihydrocapsiate etc., hereinafter sometimes to be simply referred to as "capsinoid" or "capsinoids") are different from capsaicinoid and do not have a pungent taste. However, they have been reported to show an immunity enhancing action, an energy metabolism activation action, oxygen consumption promoting action and the like (e.g., patent documents 1 and 2, and non-patent document 2), and are expected to be starting materials for food and nutritive supplements and related products in the future.

In most chili peppers, vanillylamine is formed from phenylalanine via ferulic acid, vanillin and related compounds, and capsaicinoid is produced from vanillyamine and branched chain fatty acid by capsaicinoid synthase (FIG. 1(*a*)). In contrast, capsaicinoid is scarcely produced in CH-19 Sweet and capsinoid is produced instead. However, the reason for this has been unknown for years.

As discussed above, capsinoids have a little pungent taste, but yet shows superior physiological activities similar to those of capsaicinoid. Therefore, future application as a starting material for supplements and related products is expected. Therefore, it is desired to clarify the biosynthesis pathway of capsinoids with the aim of breeding and development of new plant varieties capable of producing capsinoids.

patent document 1: JP-A-11-246478
patent document 2: JP-A-2001-026538
non-patent document 1: Yazawa et al., Journal of the Japanese Society for Horticultural Science, vol. 58, pages 601-607, 1989
non-patent document 2: Biosci. Biotech. Biochem., 65 (12), 2735-2740 (2001)

SUMMARY OF THE INVENTION

It is an object of the present invention to clarify the biosynthesis pathway of capsinoids and, based on that finding, provide a plant capable of producing capsinoids by genetic modification from a plant other than CH-19 Sweet currently known to produce capsinoids.

The present inventors have conducted intensive studies to achieve the above-mentioned object and found that, in CH-19 Sweet, pAMT gene encoding aminotransferase that catalyzes an amino group conversion reaction from vanillin to vanillylamine contains an insertional mutation. That is, it has been clarified as regards CH-19 Sweet that a stop codon is produced due to an insertional mutation of one base in the coding region of pAMT gene of pungent variety "CH-19 Hot", which is a parental variety thereof, and a functional aminotransferase is not produced. The present inventors made a hypothesis that, as a result of the mutation of the pAMT gene, a reduction reaction from vanillin to vanillyl alcohol becomes dominant in CH-19 Sweet instead of the amino group conversion from vanillin to vanillylamine, and a further esterification reaction with branched chain fatty acid results in capsinoids production (FIG. 1(*b*)).

To verify the hypothesis, the present inventors have prepared transgenic plants having a pAMT antisense nucleic acid introduced into a pungent variety, *Capsicum annuum* variety 'Takanotsume'. It has been found that production of capsaicinoid decreases but production of capsinoid markedly increases in a lineage showing remarkably decreased expression of pAMT gene from among the obtained transgenic plants.

Furthermore, present inventors have found that some mildly-pungent cultivars of *Capsicum chinense* containing high levels of capsinoid cannot produce an active pAMT due to the insertion of a transposal element into an intron of the pAMT gene resulting in abnormal splicing, which demonstrates that artificial insertion of a transposal element into the pAMT gene is also useful for preparing transgenic plants that produce high levels of capsinoid.

The present inventors have conducted further studies based on these findings and completed the present invention.

Accordingly, the present invention provides the following:

[1] a genetically modified plant capable of producing capsinoids, which shows a decreased expression or activity of an enzyme that catalyzes an amino group conversion reaction from vanillin to vanillylamine as compared to wild strains;

[2] the plant described in the above-mentioned [1], wherein the aforementioned enzyme is a pAMT gene product;

[3] the plant described in embodiments [1] or [2] described is above, wherein the aforementioned decreased expression or activity of the enzyme is caused by a destruction or mutation of the enzyme gene, a decomposition or suppressed translation of a transcription product of the gene, or inhibition of action of the enzyme on vanillin;

[4] the plant described in any of embodiments [1] to [3] described above, wherein the wild strain has a capsaicinoid biosynthesis system;

[5] the plant described in the embodiment [4] described above, wherein the wild strain is a plant belonging to the genus *Capsicum;*

[6] a method of producing a genetically modified plant capable of producing capsinoids, comprising performing a genetic modification to decrease expression or activity of an enzyme that catalyzes an amino group conversion reaction from vanillin to vanillylamine in a plant having a capsaicinoid biosynthesis system;

[7] the method described in embodiment [6] described above, wherein the genetic modification is selected from the group consisting of an introduction of DNA encoding an antisense RNA, iRNA, ribozyme or dominant-negative mutant for the aforementioned enzyme gene, a destruction of the gene by a knockout method, mutagen treatment or transposon insertion, and an introduction of a gene encoding an antibody against the enzyme;

[8] the method described in embodiment [6] or [7] described above, wherein the aforementioned enzyme is a pAMT gene product;

[9] the method described in any of the embodiments [6] to [8] described above, wherein the plant having a capsaicinoid biosynthesis system belongs to the genus *Capsicum*; and

[10] a method of producing capsinoid, comprising recovering the capsinoid from a fruit of the plant described in any of the embodiments [1] to [5] described above.

The present invention also provides the plant according to any of the embodiments described above, wherein the enzyme is an aminotransferase which catalyzes the conversion of vanillin to vanillylamine.

The present invention also provides the plant according to any of the embodiments described above, wherein the production of capsaicinoid decreases and production of capsinoid increases as compared to the wild type strain.

The present invention also provides the plant according to any of the embodiments described above, which has decreased expression of a pAMT gene.

The present invention also provides the plant according to any of the embodiments described above, which contains a pAMT antisense nucleic acid.

The present invention also provides the plant according to any of the embodiments described above, which cannot produce an active pAMT due to the insertion of a transposal element into an intron of the pAMT gene.

The present invention also provides the plant according to any of the embodiments described above, which contains an artificial insertion of a transposal element into the pAMT gene. These following embodiments are also provided by the present invention:

[a] A genetically modified plant, which has decreased expression or activity of an enzyme that catalyzes an amino group conversion reaction from vanillin to vanillylamine and an an increased capability to produce capsinoids, as compared to the corresponding wild type strain.

[b] The plant according to any of the embodiments described above, wherein the enzyme is a pAMT gene product.

[c] The plant according to any of the embodiments described above, wherein the decreased expression or activity of the enzyme is caused by a destruction or mutation of the enzyme gene, a degradation or suppressed translation of a transcript of the gene, or inhibition of action of the enzyme on vanillin (excluding insertional mutation of one nucleotide that produces a stop codon in the coding region of pAMT gene of CH-19 Sweet).

[d] The plant according to any of the embodiments described above, wherein the corresponding wild type strain has a capsaicinoid biosynthesis system.

[e] The plant according to any of the embodiments described above, wherein the corresponding wild type strain is a plant belonging to the genus *Capsicum*.

[f] The plant according to any of the embodiments described above, wherein the enzyme is an aminotransferase which catalyzes the conversion of vanillin to vanillylamine.

[g] The plant according to any of the embodiments described above, which has a decreased capability to produce of capsaicinoids as compared to corresponding wild type strain.

[h] The plant according any of the embodiments described above, which has decreased expression of a pAMT gene.

[i] The plant according to any of the embodiments described above, which contains a pAMT antisense nucleic acid.

[j] The plant according to any of the embodiments described above, which cannot produce an active pAMT due to the insertion of a transposal element into an intron of the pAMT gene.

[k] The plant according to any of the embodiments described above, which contains an artificial insertion of a transposal element into the pAMT gene.

[l] A method of producing a genetically modified plant having an increased capability to produce capsinoids, comprising performing a genetic modification to decrease expression or activity of an enzyme that catalyzes an amino group conversion reaction from vanillin to vanillylamine in a plant having a capsaicinoid biosynthesis system.

[m] The method according to any of the embodiments described above, further comprising selecting a plant showing an increased amount of capsinoids production as compared to that of the corresponding non-genetically modified plant.

[n] The method according to any of the embodiments described above, wherein the genetic modification is selected from the group consisting of an introduction of DNA encoding an antisense RNA, iRNA, ribozyme or dominant-negative mutant for the aforementioned enzyme gene, a destruction of the gene by a knockout method, mutagen treatment or transposon insertion, and an introduction of a gene encoding an antibody against the enzyme.

[o] The method according to any of the embodiments described above, wherein the enzyme is a pAMT gene product.

[p] The method according to any of the embodiments described above, wherein the plant having a capsaicinoid biosynthesis system belongs to the genus *Capsicum.*

[q] The method according to any of the embodiments described above, wherein the enzyme is an aminotransferase which catalyzes the conversion of vanillin to vanillylamine.

[r] A method of producing capsinoid, comprising recovering the capsinoid from a fruit of the plant according to any of the embodiments described above.

The present invention provides increased production of capsinoids also in a plant variety that substantially does not produce capsinoids or produces only a small amount thereof.

DETAILED DESCRIPTION OF THE INVENTION

Figure 1:
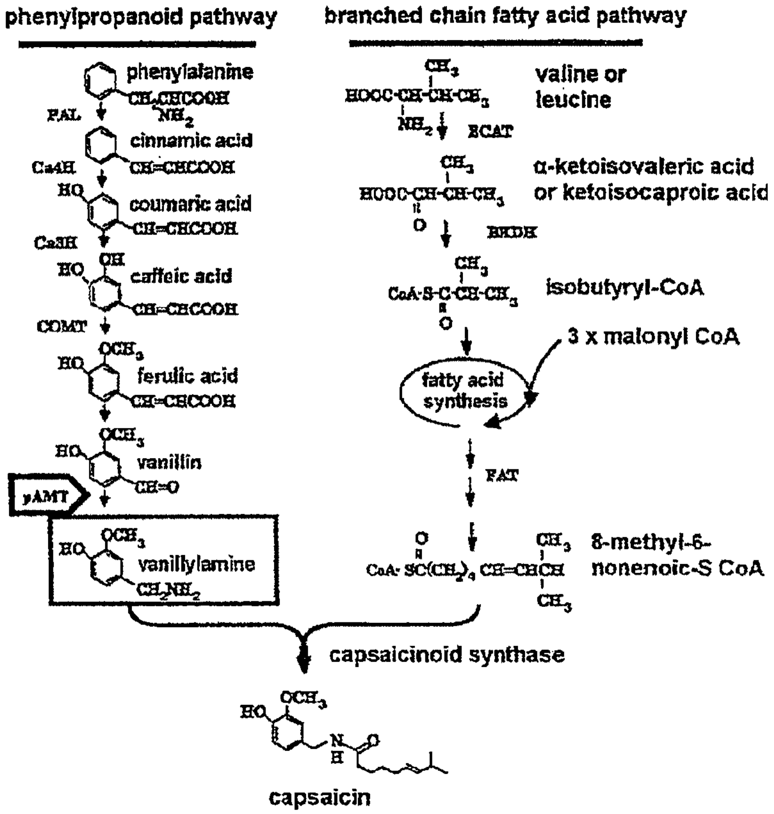
FIG. 1 shows expected synthesis pathways of capsaicin (*a*) and capsiate (*b*).
Figure 1:
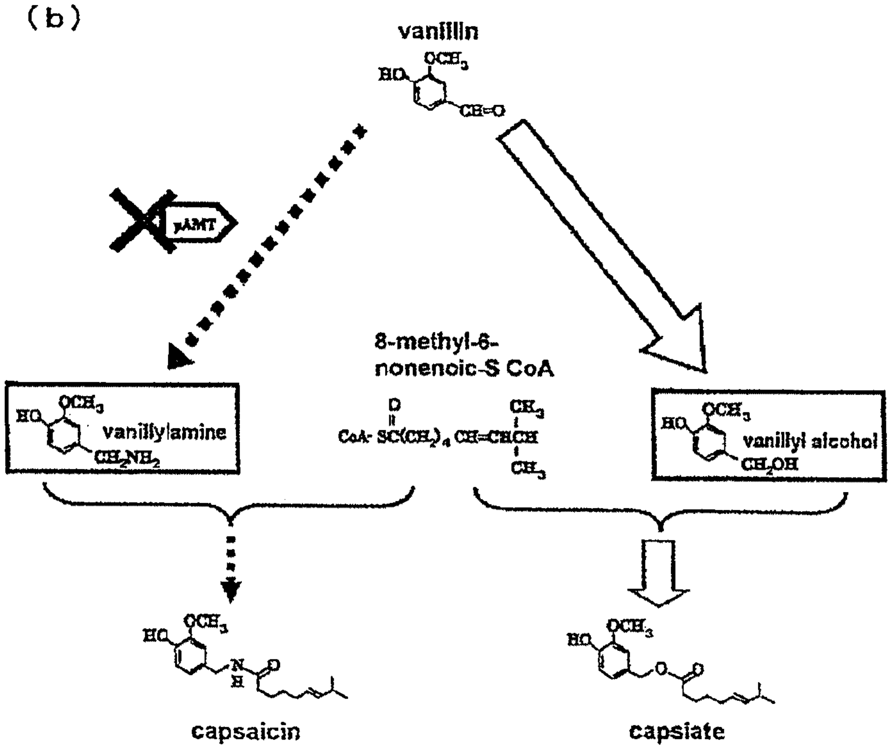

The present invention provides a genetically modified plant capable of producing capsinoids as compared to wild strains, which shows a decreased expression or activity of an enzyme that catalyzes an amino group conversion reaction from vanillin to vanillylamine.

In the present invention, the "wild strain" means a plant to be the target of genetic modification in the present invention. The wild strain to be used in the present invention may be any as long as it functionally expresses enzyme group (e.g., phenylalanineammonialyase (PAL), cinnamic acid 4-hydrolase (Ca4H), coumaric acid 3-hydrolase (Ca3H), caffeic acid O-methyltransferase (COMT), capsaicinoid synthase (CS)) necessary for biosynthesis of capsaicinoid. The plant may have such enzyme group by nature, or one or more enzymes may be provided by the expression of a foreign gene. Preferably, the wild strain that can be used for the present invention is a plant having capsaicinoid production ability by nature, more preferably, plants belonging to *Capsicum*. Examples of thereof include, but are not limited to, *C. annuum* (variety 'Takanotsume', CH-19 Hot, Yatsufusa', 'Toranoo', 'Fushimiama', and the like), *C. baccatum* (aji amarillo and the like), *C. chinense* (habanero pepper, Bhut Jolokia and the like), *C. frutescens* (*Capsicum frutescens* L. and the like), and *C. pubescens* (rocoto and the like).

An enzyme that catalyzes an amino group conversion reaction from vanillin to vanillylamine is not particularly limited as long as it is a protein having an aminotransferase activity and produced by the above-mentioned wild strain, which can use vanillin as a substrate. Preferred are aminotransferase pAMT (Putative Aminotransferase) gene having high homology with GABA aminotransferase from rice or tomato, which was found in habanero pepper, and aminotransferase encoded by its ortholog in other plant variety.

More specifically, pAMT protein (also referred to as pAMT gene product) of the present invention is a protein containing the same or substantially the same amino acid sequence as the amino acid sequence shown by SEQ ID NO: 2, and having an aminotransferase activity at least equivalent (e.g., 0.5-fold or more, preferably 0.7-fold or more) to the protein consisting of the amino acid sequence shown by SEQ ID NO: 2. Here, the "substantially the same amino acid sequence" means an amino acid sequence of natural allele variant or gene polymorphism of pAMT protein derived from CH-19 Hot consisting of the amino acid sequence shown by SEQ ID NO: 2, and an amino acid sequence of its ortholog in other plant variety and the like. Examples of the ortholog of pAMT in other plant variety include pAMT derived from habanero pepper (Refseq No. AAC78480), GABA aminotransferase from rice (Refseq No. AAQ14479) and GABA aminotransferase from tomato (Refseq No. AAO92257) and the like can be mentioned.

The above-mentioned "substantially the same amino acid sequence" desirably has not less than 80%, preferably not less than 90%, more preferably not less than 95%, most preferably not less than 97%, of similarity (preferably, identity) to the amino acid sequence shown by SEQ ID NO: 2. The "similarity" here means, when two amino acid sequences were aligned using mathematical algorithm known in the art, a proportion (%) of the same and similar amino acid residues to the total overlapping amino acid residues in an optimal alignment (preferably, the algorithm can consider introduction of gap(s) into one or both of the sequences for an optimal alignment). The similarity of amino acid sequences in the present specification can be calculated using homology calculation algorithm NCBI BLAST (National Center for Biotechnology Information Basic Local Alignment Search Tool) under the following conditions (expectancy=10; allow gap; matrix=BLOSUM62; filtering=OFF).

In the present invention, an enzyme group of capsinoid biosynthesis system is at least partly common with an enzyme group constituting a capsaicinoid biosynthesis system, except those that catalyze the reduction reaction from vanillin to vanillyl alcohol, and the present invention is based on the finding that the quantitative ratio of the produced capsinoid and capsaicinoid depends on which of the above-mentioned reduction reaction and an amino group conversion reaction from vanillin to vanillylamine proceeds more dominantly. Therefore, by lowering the expression or activity of an enzyme that catalyzes an amino group conversion reaction from vanillin to vanillylamine than that of wild strains, the reduction reaction from vanillin to vanillyl alcohol becomes more dominant and, as a result, the capsinoid production capability can be improved.

The "expression" of an enzyme that catalyzes an amino group conversion reaction from vanillin to vanillylamine means that a translation product (i.e., protein) is produced by a gene encoding the enzyme (e.g., pAMT gene etc.), and is localized at the action site thereof in a functional state. The "lower expression" of an enzyme means a result of a significantly decreased protein amount of the enzyme present in a genetically modified plant, as compared to that of wild strain. Therefore, a genetic modification to lower enzyme expression can be performed in any stage, for example, at a gene level, transcription level, post-transcription regulation level, translation level, post-translational modification level and the like.

For example, as a genetic modification that suppresses enzyme expression at a gene level, destruction of the enzyme gene and introduction of functionally defective mutation can be mentioned. Here, the "functionally defective mutation" may be a mutation that decreases the enzyme activity such that the capsinoid production increases significantly as compared to wild strains, and a mutation that completely eliminates the enzyme activity is not necessarily intended. Such genetic modification can be achieved by a knockout (or knockin) technique of an enzyme gene utilizing a homologous recombination.

As a specific means to knockout an enzyme gene, a method including isolating an enzyme gene (genome DNA) derived from a plant to be a target of genetic modification (i.e., wild strain) by a conventional method (e.g., in the case of a pAMT gene, pAMT genome DNA can be cloned by a colony or plaque hybridization method from genome DNA library prepared from genomic DNA isolated from a wild strain, using a nucleic acid containing whole or part of the base sequence of CH-19 Hot-derived pAMT cDNA shown by SEQ ID NO: 1 as a probe) and inserting a DNA chain (targeting vector) having a DNA sequence constructed to inactivate the gene into the enzyme gene locus of a wild strain by homologous recombination and the like can be preferably used. A DNA chain (targeting vector) having a DNA sequence constructed to inactivate the gene is prepared by, for example, (1) inserting other DNA fragment (e.g., selection marker gene of drug resistance gene, reporter gene and the like) into the exon region or promoter region thereof to destroy the exon or promoter function, (2) cleaving out whole or part of the enzyme gene by using the Cre-loxP system or Flp-frt system to delete the gene, (3) inserting a stop codon into a protein coding region to prevent complete translation of protein, or (4) inserting a DNA sequence (e.g., polyadenylated signal and the like) that terminates gene transcription into a transcription region to prevent synthesis of complete mRNA.

The selection marker gene is preferably in the form of an expression cassette containing any promoters capable of intracellularly functioning in a target plant. When the gene is inserted such that it is placed under control of an endogenous promoter of the target enzyme gene, a selection marker gene does not require a promoter.

Generally, gene recombination in plant is mostly nonhomologous, and introduced DNA is randomly inserted into any position of chromosome. Therefore, efficient selection of only a clone targeted to an enzyme gene by homologous recombination, cannot be achieved on the basis of selection of detection of drug resistance, expression of reporter gene and the like. Thus, confirmation of recombination site of any selected clone by Southern hybridization method or PCR method becomes necessary. Thus, when, for example, the Herpes simplex virus-derived thymidine kinase (HSV-tk) gene that imparts gancyclovir sensitivity is ligated outside the region homologous to the target sequence in a targeting vector, a cell having the vector randomly inserted therein has an HSV-tk gene, and therefore, the cell cannot grow in a medium containing gancyclovir. However, a cell targeted to an enzyme gene locus by homologous recombination becomes gancyclovir resistant since it does not have an HSV-tk gene and can be selected. Alternatively, when, for example, a diphtheria toxin gene is ligated instead of the HSV-tk gene, since a cell having the vector randomly inserted therein is killed by the toxin it produces, a homologous recombinant can also be selected in the absence of a drug. The presence of introduced DNA can be confirmed by applying a part of the formed resistant colony to PCR or Southern hybridization.

As another genetic modification to suppress enzyme expression at a gene level, introduction of a functionally defective mutation into an enzyme gene by a mutagen treatment or introduction of a nucleic acid containing a tranposal element can be mentioned. As the mutagen treatment, any can be used as long as it induces point mutation, deletion or frame shift mutation in the DNA of a wild strain. Specifically, treatments with ethylnitrosourea, nitrosoguanidine, benzopyrene, acridine dye, radiation and the like can be mentioned. In addition, various alkylating agents and carcinogens can also be used as mutagens. As a method of reacting a mutagen with a cell, the method described in Technique of Tissue Culture, 3rd edition (Asakura Publishing Co., Ltd.), The Japan Tissue Culture Association ed. (1996), Nature Genet., 314 (2000) and the like can be used. As the transposal element, any known heterologously functional transposal elements such as Ac/Ds from *Zea mays*, or an endogenous transposal element of *Capsicum chinense* ($T_{cc}$) identified in the present invention can be mentioned. These transposal elements can be introduced into target plant cells by any known gene delivery methods such as electroporation, PEG-method and particle bombardment. Non-autonomous transposal elements that do not encode a transposase such as Ds or $T_{cc}$ can be co-introduced with a nucleic acid encoding a transposase capable of acting in trans. The transposal element may be inserted into not only an exon but also an intron of pAMT gene. The insertion into an intron may cause abnormal splicing resulting in the generation of an inactive pAMT translation product. The transposal element inserted into the pAMT gene can be excised insofar as the excision generates a footprint resulting in a frameshift mutation.

A functionally defective variant of an enzyme gene can be selected using the amount of target protein as an index. In the case of pAMT, for example, Western blot analysis can be performed using a polyclonal antibody to pAMT protein, and the amount of the pAMT protein can be determined. As for a plant showing a significantly decreased pAMT protein level, introduction of a mutation into the gene can be confirmed by determining the nucleotide sequence of the enzyme gene isolated from a part of the plant.

As a genetic modification to suppress enzyme expression at a translation level, introduction of a nucleic acid having an activity to degrade a transcription product of an enzyme gene, or a nucleic acid that suppresses translation of a transcription product into an enzyme protein can be mentioned. As such nucleic acid, a nucleic acid containing a nucleotide sequence complementary or substantially complementary to the nucleotide sequence of mRNA of the enzyme, or a part of the sequence, can be mentioned.

The nucleotide sequence substantially complementary to the nucleotide sequence of mRNA of a target enzyme means a nucleotide sequence having complementation of the level capable of binding to the target sequence of the mRNA and inhibiting the translation thereof under physiological conditions in the subject plant. Specifically, for example, a nucleotide sequence having a similarity of not less than about 80%, preferably not less than about 90%, more preferably not less than about 95%, most preferably not less than about 97%, to the region overlapping with a nucleotide sequence completely complementary to the nucleotide sequence of the mRNA (i.e., nucleotide sequence of mRNA complementary chain). The "similarity of nucleotide sequence" in the present invention can be calculated using homology calculation algorithm NCBI BLAST (National Center for Biotechnology Information Basic Local Alignment Search Tool) and under the following conditions (expectancy=10; allow gap; filtering=ON; match score=1; mismatch score=−3).

More specifically, for example, when the enzyme is pAMT, examples of a nucleotide sequence complementary or substantially complementary to the nucleotide sequence of pAMT mRNA include (a) the nucleotide sequence shown by SEQ ID NO: 1 or (b) a nucleotide sequence that hybridizes to the nucleotide sequence under stringent conditions, which is a nucleotide sequence complementary or substantially complementary to a sequence encoding a protein having an activity equivalent to that of a protein consisting of the amino acid sequence shown by SEQ ID NO: 2. Under stringent conditions means, for example, the conditions described in Current Protocols in Molecular Biology, John Wiley & Sons, 6.3.1-6.3.6, 1999, for example, hybridization with 6×SSC (sodium chloride/sodium citrate)/45° C., then washing one or more times with 0.2×SSC/0.1% SDS/50-65° C. and the like, and those of ordinary skill in the art can appropriately select hybridization conditions affording stringency equivalent thereto.

pAMT mRNA is preferably pAMT mRNA of CH-19 Hot containing the nucleotide sequence shown by SEQ ID NO: 1, or ortholog thereof in other plant variety (e.g., habanero pepper-derived pAMT (Refseq No. AF085149), GABA aminotransferase of rice (Refseq No. AF297651) and GABA aminotransferase of tomato (Refseq No. AY240231) etc.), or further, natural allele variant, or gene polymorphism thereof.

The "part of a nucleotide sequence complementary or substantially complementary to nucleotide sequence of mRNA of a target enzyme" is not particularly limited in terms of length and position, as long as it can specifically bind to target enzyme mRNA and inhibit translation of protein from the mRNA. From the aspect of sequence specificity, however, it contains at least 10 bases, preferably not less than about 15 bases, more preferably not less than about 20 bases, of a part complementary or substantially complementary to the target sequence.

Specifically, preferable examples of the nucleic acid containing a nucleotide sequence complementary or substantially complementary to a nucleotide sequence of mRNA of a target enzyme, or a part of such sequence, include the following (a) to (c).

(a) antisense RNA to target enzyme mRNA (b) iRNA (interfering RNA) to target enzyme mRNA (c) ribozyme to target enzyme mRNA (a) Antisense RNA to Target Enzyme mRNA The "antisense RNA" in the present invention is a nucleic acid containing a nucleotide sequence complementary or substantially complementary to the nucleotide sequence of target mRNA, or a part thereof, and has a function to suppress protein synthesis by forming a specific and stable double strand with target mRNA. The target region of antisense RNA is not particularly limited in terms of length, as long as hybridization of the antisense RNA results in the inhibition of translation of target mRNA into an enzyme protein, and it may be the total mRNA sequence encoding the enzyme or a partial sequence thereof, wherein a shorter one is about 10 bases long and a longer one is the total mRNA sequence.

Moreover, the antisense RNA of the present invention may not only hybridize to target enzyme mRNA to inhibit translation into a protein, but also be bound to a gene of the enzyme, which is a double stranded DNA, to form a triplex and inhibit transcription to RNA (anti-gene).

(b) iRNA to Target Enzyme mRNA

In the present specification, a double stranded RNA consisting of oligoRNA complementary to target enzyme mRNA and a complementary chain thereof, i.e., iRNA, is also defined to be encompassed in the nucleic acid containing a nucleotide sequence complementary or substantially complementary to a nucleotide sequence of mRNA of a target enzyme, or a part thereof. A phenomenon of intracellular introduction of a double stranded RNA resulting in degradation of mRNA complementary to RNA thereof, so-called RNA interference (RNAi), has long been known in nematode, insect, plant and the like. Ever since this phenomenon was confirmed to widely occur in is animal cells [Nature, 411(6836): 494-498 (2001)], it has been widely used as an alternative technique of ribozyme. iRNA can be appropriately designed based on the information of nucleotide sequence of mRNA to be the target and using commercially available software (e.g., RNAi Designer; Invitrogen).

(c) Ribozyme to Target Enzyme mRNA

As ribozyme with broadest utility, self-splicing RNA seen in infectious RNA such as viroid, virusoid and the like can be mentioned, and hammerhead type, hairpin type and the like are known. The hammerhead type shows enzyme activity with only about 40 bases, and it is possible to specifically cleave target mRNA alone by rendering several bases on both ends (about 10 bases in total) adjacent to the part with a hammerhead structure form a sequence complementary to a desired cleavage site of mRNA. Since this type of ribozyme contains RNA alone as a substrate, it is further advantageous since it does not attack genomic DNA. When target enzyme mRNA itself has a double stranded structure, the target sequence can be converted to a single strand by using a hybrid ribozyme wherein virus nucleic acid-derived RNA motif capable of specifically binding to RNA helicase is ligated [Proc. Natl. Acad. Sci. USA, 98(10): 5572-5577 (2001)]. Moreover, to promote transfer to the cytoplasm, a hybrid ribozyme wherein a sequence obtained by modifying tRNA is further ligated may be used [Nucleic Acids Res., 29(13): 2780-2788 (2001)].

A DNA encoding an antisense RNA to mRNA of target enzyme, when the antisense RNA is comparatively long and is, for example, not less than 100 bp, can be produced by cloning cDNA of the target enzyme according to a conventional method, and directly ligating same, or ligating after fragmentation into a desired length containing a desired region by digestion with a suitable restriction enzyme, to the downstream of a promoter capable of functioning in the cell of the target plant, in an antisense direction. When the antisense RNA is comparatively short and is, for example, 100 bp or below, it can also be chemically synthesized by a commercially available DNA/RNA automatic synthesizer.

DNA encoding IRNA to target enzyme mRNA can be constructed as a DNA encoding hairpin type dsRNA by amplifying the target sequence (for example, about 200-500 bases) on mRNA by RT-PCR to give double stranded DNA, and ligating two double stranded DNAs in the sense direction and antisense direction via suitable linker sequences by using restriction enzyme and ligase. The linker sequence is not particularly limited in terms of its sequence and length as long as it can form a loop capable of forming a hairpin type dsRNA on transcription of the constructed DNA. For example, when a reporter gene such as β-glucuronidase gene is used as a linker sequence, cutting out iRNA from the hairpin type dsRNA can be monitored by detection of the expression of the reporter gene.

The DNA encoding ribozyme to target enzyme mRNA can be prepared by synthesizing a DNA having a nucleotide sequence of designed ribozyme by a DNA/RNA automatic synthesizer.

A nucleic acid containing a nucleotide sequence complementary or substantially complementary to a nucleotide sequence of mRNA of a target enzyme, or a part thereof, may be introduced into a target plant by any genetic engineering method. For example, infection with a plant virus containing a virus genome genetically engineered to contain the nucleic acid, and transformation of a target plant cell with an expression vector containing the nucleic acid can be mentioned.

Preferably, the genetically modified plant of the present invention is a transgenic plant obtained by transforming the cell of the wild strain with an expression vector containing the above-mentioned nucleic acid under control of a promoter capable of functioning in a target plant (wild strain) cell.

The promoter capable of functioning in a wild strain cell can be appropriately selected according to the plant variety used as the wild strain. Generally, a gene promoter constitutionally expressed in a plant cell, preferably constitutional promoter derived from a plant or plant virus (e.g., Cauliflower mosaic virus (CaMV) 35S promoter, CaMV 19S promoter, NOS promoter etc.), or cis promoter in a wild strain target enzyme gene and the like can be mentioned.

In the expression vector of the present invention, a nucleic acid containing a nucleotide sequence complementary or substantially complementary to a nucleotide sequence of mRNA of a target enzyme, or a part thereof is located at the downstream of a promoter capable of functioning in a wild strain cell, so that transcription thereof can be regulated by the promoter. It is preferable that a transcription termination signal (terminator region) capable of functioning in a wild strain be further added at the downstream of the nucleic acid sequence. Examples of the terminator include NOS (nopalinesynthase) gene terminator and the like.

The expression vector of the present invention may further contain a cis-regulatory element such as an enhancer sequence and the like. Moreover, the expression vector desirably further contains a marker gene for selection of a transformant such as a drug resistance gene marker and the like [e.g., neomycin phosphotransferase II (NPTII) gene, hygromycin phosphotransferase (HPT) phosphinothricinacetyltransferase (PAT) gene, glyphosate resistance gene and the like.

To facilitate large-scale preparation and purification, moreover, the expression vector desirably contains a replication origin that enables autonomous replication in *Escherichia coli* and a selection marker gene in *Escherichia coli* (for example, ampicillin resistance gene, tetracycline resistance gene etc.). The expression vector of the present invention can be conveniently constructed by inserting an expression cassette of the above-mentioned nucleic acid and, where necessary, a selection marker gene into a cloning site of a pUC or pBR *Escherichia coli* vector.

When the above-mentioned nucleic acid is introduced by utilizing infection with *Agrobacterium tumefaciens* or *Agrobacterium rhizogenes*, an expression cassette of the nucleic acid can be inserted into the T-DNA region (region to be transferred to plant chromosome) on Ti or Ri plasmid retained by the bacterium, and put to use. For a standard method of transformation by *Agrobacterium* method, a binary vector system is used. The function necessary for T-DNA transfer is independently supplied by both T-DNA itself and Ti (or Ri) plasmid, and each constituent factor can be divided on different vectors. A binary plasmid has a 25 bp border sequence on both ends necessary for cutting out and insertion of T-DNA, and is free of a plant hormone gene causing crown gall (or hairy root), thus simultaneously affording a room for insertion of a foreign gene. As such binary vector, for example, pBI101, pBI121 (both CLONTECH) and the like are commercially available. The vir region that acts on insertion of T-DNA is located on a different Ti (or Ri) plasmid called a helper plasmid.

Conventionally known various methods can be used for transformation of plants. Examples thereof include a method including isolating protoplast from a cell of a target plant by a treatment with a cell wall degrading enzyme such as cellulose, hemicellulose and the like, and adding polyethylene glycol to a suspension of the protoplast and an expression vector containing the above-mentioned pAMT gene expression cassette to insert the expression vector into the protoplast by an endocytosis-like process (PEG method), a method including inserting an expression vector into a lipid membrane vesicle such as phosphatidylcholine and the like by sonication and the like, and fusing the vesicle and protoplast in the presence of PEG (liposome method), a method including fusion by a similar process using a mini-cell, and a method including applying an electric pulse to a suspension of protoplast and expression vector to insert the vector in the extracellular solution into the protoplast (electroporation method). However, these methods are complicated since a culture technique for redifferentiation from the protoplast to a plant is necessary. As methods of transgene into an intact cell having a cell wall, a microinjection method including pushing a micropipette into a cell, and intracellularly injecting a vector DNA in the pipette by hydraulic pressure or gas pressure, a direct introduction method including accelerating metal microparticles coated with DNA by powder explosion or gas pressure for intracellular introduction such as a particle gun method and the like, and a method utilizing infection with *Agrobacterium* can be mentioned. Microinjection has a defect in that the operation requires practice, and the number of handleable cells is small. Considering the convenience of operation, therefore, plant is preferably transformed by an *Agrobacterium* method or a particle gun method. The particle gun method is further useful since a gene can be directly introduced into the apical meristem of a plant before harvesting. Moreover, in the *Agrobacterium* method, by simultaneously inserting a plant virus, for example, genomic DNA of geminivirus such as tomato golden mosaic virus (TGMV) and the like between border sequences of a binary vector, virus infection spreads over the whole plant by merely inoculating a cell suspension with a syringe barrel and the like to a cell at any part of a plant before harvesting, and an object gene is simultaneously introduced into the whole plant.

In the particle gun method and *Agrobacterium* method, however, since transgene is often chimeric, a sample cell that permits introduction of the above-mentioned nucleic acid into a germ line cell at high frequency needs to be used for transformation. For example, embryo, hypocotyl piece, embryogenic callus, isolated growing point and the like can be mentioned. On the other hand, since the above-mentioned transformation method using protoplast and microinjection method permit selection of a redifferentiation plant from a single cell, they are superior transformation means for obtaining a homogeneous transgenic plant having a pAMT gene introduced into the whole cell.

As specific examples, introduction of an object nucleic acid by *Agrobacterium* and regeneration method of transformed cell into a plant in a *Capsicum* plant are shown in the following, which are mere examples and do not at all limit the production method of the genetically modified plant of the present invention.

A seed of a chili pepper plant is sterilized, sown on a suitable seed germination medium (e.g., MS medium, LS medium, B5 medium and the like), and aseptically grown. On the other hand, *Agrobacterium* having a promoter connected with an object nucleic acid, and transformed with a plasmid having a kanamycin resistance gene and a hygromycin resistance gene is cultured, and diluted with a suitable medium to give an *Agrobacterium* solution. Cotyledon after germination is immersed in the *Agrobacterium* solution for about 10 min, transplanted to a selection medium (e.g., MS medium, LS medium, B5 medium and the like) added with a desired plant hormone (e.g., auxins such as IAA, NAA and the like, cytokinins such as kinetin, benzyladenine and the like) and kanamycin and hygromycin antibiotics, and cultivated at 20-30° C. The obtained kanamycin and hygromycin resistant callus and seedling are transplanted to a redifferentiation (rooting) medium (e.g., MS medium, LS medium, B5 medium and the like) added with benzyladenine as necessary to induce redifferentiation (rooting), whereby a seedling plant is obtained. When several true leaves are observed, the seedling plant is transplanted to the soil for acclimation, and grown in a controlled greenhouse such as biotron and the like. Seed and fruit can be obtained from the thus-obtained transformant.

The genomic DNA is extracted from the above-mentioned transformant according to a conventional method, the DNA is cleaved with a suitable restriction enzyme, and Southern hybridization is performed using the introduced object nucleic acid as a probe, whereby the presence or absence of transformation can be confirmed. In addition, the presence or absence of transformation can also be confirmed by synthesizing a primer that specifically amplifies the object nucleic acid and performing a PCR method.

Moreover, RNA can be extracted from a transformant or untransformant by a conventional method, and changes in the expression level of target enzyme mRNA can be examined by quantitative RT-PCR, Northern hybridization and the like. Alternatively, a protein can be extracted from a transformant or untransformant by a conventional method, and changes in the expression level of target enzyme protein can be examined by immunoassay (RIA method, ELISA method, FIA method and the like) by using an antibody to the target enzyme. As mentioned above, since most of the gene recombination events in plants result from nonhomologous recombination, the expression of target enzyme does not always decrease in all transgenic plants as compared to wild strains, due to the position effect of chromosome region inserted with the introduced nucleic acid. Therefore, as mentioned above, by measuring and comparing the expression amounts of transformant and untransformant at RNA level or protein level of the target enzyme, lower expression of the target enzyme in a transgenic plant than in a wild strain can be confirmed, based on which the object genetically modified plant can be obtained.

Plants differentiated from a seed obtained by self-fertilization of the thus-obtained transgenic plants, which show lower expression of the target enzyme as compared to wild strains and, as a result, show higher capsinoid production capability as compared to wild strains are statistically contained at a certain ratio according to the insertion manner of the object nucleic acid. The appearance ratio of the improved capsinoid production capability in plants differentiated from the R1 seed obtained by self-fertilization of a redifferentiated generation (R0) plant generally follows the Mendel's Law. For example, when the object nucleic acid is heterozygously inserted into one gene locus, R1 seeds are divided into 3:1 based on the improved capsinoid production capability. Among the R1 plants differentiated from the R1 seed, those having improved capsinoid production capability are grown and self-fertilized to give R2 seeds. When the improved capsinoid production capability is maintained in all seeds, the R1 plant is determined a homozygote for the introduced nucleic acid, and when the improved capsinoid production capability is shown in 3:1, the R1 plant is determined to be a heterozygote for the introduced nucleic acid. The thus-selected, genetically modified plant which is a homozygote for the introduced nucleic acid is extremely useful as a strain fixedly having an improved capsinoid production capability. Since capsinoid is accumulated in a fruit (fruit skin, placenta and the like), the capsinoid production capability can be known at an earlier stage by desirably using, as an index, expression or activity of a target enzyme which is also expressed in a tissue such as leaf and the like.

The genetic modification that inhibits activity of an enzyme that catalyzes an amino group conversion reaction from vanillin to vanillylamine is not particularly limited as long as it is known. For example, introduction of an antibody gene to the enzyme, introduction of a dominant-negative mutant gene, and the like can be mentioned.

To avoid difficulties such as assembly efficiency of H chain and L chain within the plant and the like, the antibody gene desirably encodes a single chain antibody prepared by genetic engineering, such as scFv, scFv-Fc, minibody, diabody and the like. Such antibody can be prepared by producing an antibody producing hybridoma from a mouse immunized with a target enzyme protein or a fragment thereof by a conventional method, cloning the antibody gene from the cell by a conventional method, and ligating the fragment via a linker DNA as appropriate.

A dominant-negative mutant refers to one with decreased activity due to the introduction of a mutation into a target enzyme. In the dominant-negative mutant, the function of the enzyme can be indirectly inhibited by competitively interacting a target endogeneous enzyme in a wild strain with the substrate vanillin. The dominant-negative mutant can be produced by introducing a mutation into the nucleic acid encoding the target gene. Examples of the mutation include amino acid mutation that causes a decrease in the function provided by a functional site (e.g., deletion, substitution or addition of one or more amino acids). A dominant-negative mutant can be produced by PCR or a method known per se using a known kit.

As a method of introducing a DNA encoding an antibody gene and dominant-negative mutant into a target plant to give a transgenic plant, a method similar to the above-mentioned methods for introducing nucleic acid containing a nucleotide sequence complementary or substantially complementary to the nucleotide sequence of mRNA of a target enzyme, or a part thereof, is preferably used.

Therefore, by measuring and comparing the activity of the target enzyme between transformant and untransformant, lower activity of the target enzyme in the obtained genetically modified plant than in a wild strain can be confirmed, based on which the object genetically modified plant can be obtained. For example, when the target enzyme is pAMT, a protein is extracted from placenta, flower and the like, vanillin is added to the extract and the mixture is incubated for a given time, and the resulting vanillylamine is quantified by HPLC and the like, whereby the enzyme activity can be examined.

The genetically modified plant obtained as mentioned above, which shows a decreased expression or activity of an enzyme that catalyzes an amino group conversion reaction from vanillin to vanillylamine as compared to a wild strain, shows increased capsinoid production capability as compared to the wild strain. The "increased production capability" may be further increased capsinoid production capability as compared to a wild strain having an ability to produce capsinoids by nature, or production capability newly acquired by a plant incapable of producing capsinoid by nature.

The present invention also provides a production method of capsinoids, including recovering capsinoids from the genetically modified plant of the present invention. As a method of recovering capsinoids, any known method may be used and, for example, the methods described in the above-mentioned patent document 1 (JP-A-11-246478), JP-A-2002-226445, JP-A-2004-018428, WO2005/122787 and/or 2006/043601 can be used unlimitatively, all incorporated herein by reference.

EXAMPLES

Example 1

Figure 2:
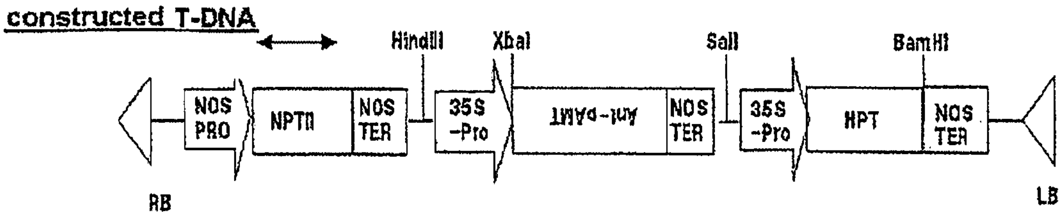
FIG. 2 is a schematic diagram of Ti-plasmid vector, pIG121-Hm, having pAMT gene inserted in the antisense direction.

Production of pAMT Gene Expression-Suppressive Transformed Chili Pepper pAMT gene amplified by RT-PCR with cDNA extracted from CH-19 Sweet was inserted into a GUS region of Ti-plasmid vector pIG121-Hm in the antisense direction (FIG. 2). The plasmid was introduced into *Agrobacterium tumefaciens* EHA101 strain and used for transformation of chili pepper.

Figure 3:
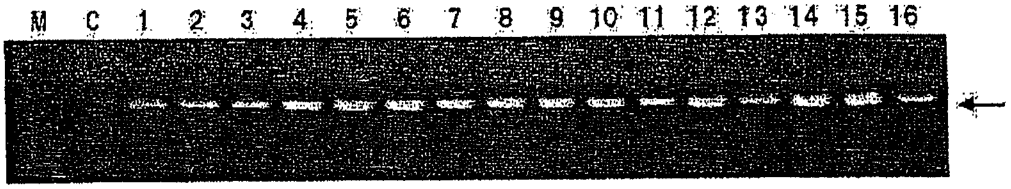
FIG. 3 shows the results of genomic PCR using DNA extracted from leaf piece(s) of transformed chili pepper as a template, wherein M is a marker, C is a control (*Capsicum annuum* variety 'Takanotsume' without genetic modification), and each number shows selected transformed chili pepper individuals.

The surface of a seed of *Capsicum annuum* variety 'Takanotsume' was sterilized with 70% ethanol for 1 min and 2% sodium hypochlorite for 15 min, rinsed 3 times with sterile water, and sown in MS medium. Cotyledon germinated 10 days later was cut and transplanted to MS medium containing 10 mg/l benzyladenine (BA). 16 hr day-length culture was performed at 25° C. for 24 hr, and the cotyledon was immersed for 10 min in *Agrobacterium* suspension cultured in YEP medium containing 50 mg/l kanamycin and 50 mg/l hygromycin for 24 hr. To remove redundant *Agrobacterium* suspension, the leaf was placed on sterilized filter paper, and then transplanted again to MS medium containing 10 mg/l benzyladenine (BA). After co-cultivation in a dark place for 3 days, the leaf was transplanted to MS medium (selection medium) containing 10 mg/l BA, 50 mg/l kanamycin and 300 mg/l carbenicillin, and 16 hr day-length culture was performed at 25° C. To suppress growth of *Agrobacterium*, the selection medium was exchanged with a new medium every 10 days-2 weeks. A shoot redifferentiated 1-2 months from the start of the selection was transplanted to MS medium (rooting medium) containing 50 mg/l kanamycin and 300 mg/l carbenicillin to induce rooting. The rooted plants of 16 strains were transplanted to soil, and grown in phytotron. DNA was extracted from leaf/leaves of the selected individual, and genomic PCR analysis was performed using a primer that amplifies NPTII gene in the vector. The PCR product was applied to 1.5% agarose gel electrophoresis, and stained with ethidium bromide. As a result, the selected individual was found to have NPTII gene introduced thereinto (FIG. 3).

Example 2

Measurement of Capsiate and Capsaicin Contents of Transformed Chili Pepper

Figure 4:
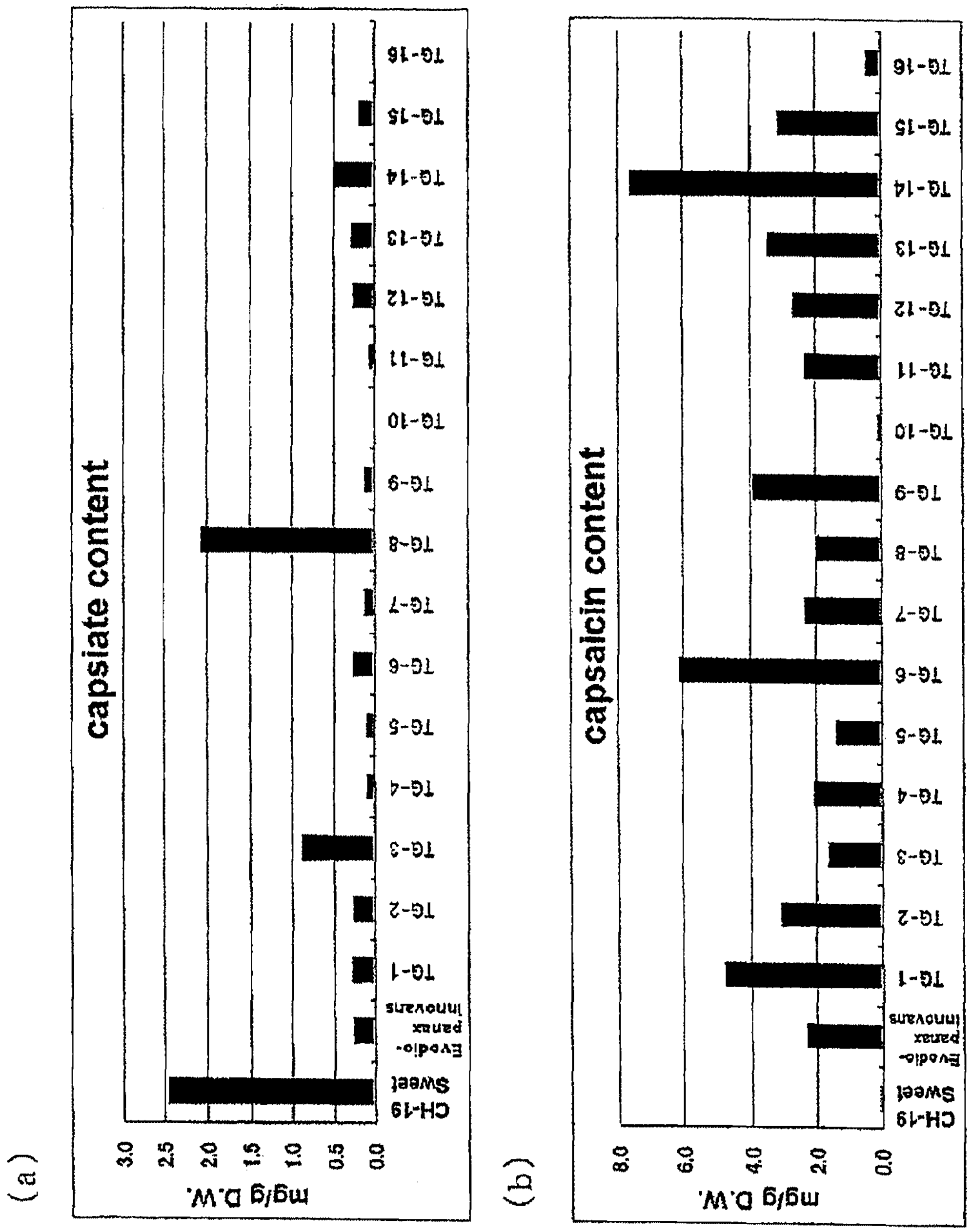
FIG. 4 shows the analytical results of capsiate content (a) and capsaicin content (b) of fruits of transformed chili pepper and CH-19 Sweet, and *Capsicum annuum* variety 'Takanotsume'.

Fruits were taken from 16 strains of transformed chili pepper and *Capsicum annuum* variety 'Takanotsume' without introduction of a gene, and capsiate and capsaicin contents were measured by a conventional method. As a result, 3 transformed chili pepper fruits (TG-3, 8 and 14) were found to contain capsiate in larger amounts than in control *Capsicum annuum* variety 'Takanotsume'. TG-3 and TG-8 had lower capsaicin contents than other strains (FIGS. 4(*a*) and 4(*b*)).

Example 3

Figure 5:
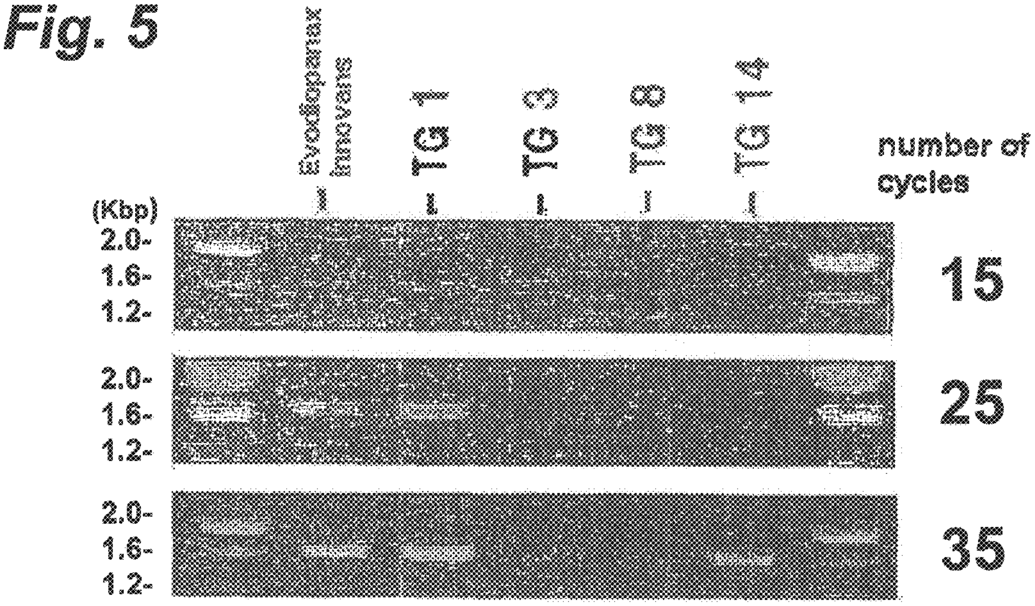
FIG. 5 shows the analytical results of transcription expression of pAMT gene in fruits of transformed chili pepper and *Capsicum annuum* variety 'Takanotsume'.

Transcription and Expression Analysis of pAMT Gene in Transformed Chili Pepper Fruit RNA was extracted from a fruit of a strain with higher capsiate content, and RT-PCR analysis of transcription amount of endogenous pAMT gene was performed. As a result, the strain with high capsiate content was found to show suppressed transcription and expression of pAMT gene. On the other hand, in a strain wherein the capsiate content was not high even though the gene had been introduced, the transcription and expression of endogenous pAMT gene was not suppressed (FIG. 5). From the above results, it has been found that a plant can be modified to artificially synthesize capsiate, by suppression of expression of pAMT gene.

Example 4

Analysis of pAMT Protein Amount in Transformed Chili Pepper Fruit

The full-length pAMT gene isolated from CH-19 Hot was inserted into a multicloning site of *Escherichia coli* expression vector (pColdI vector, Takara Bio Inc.). The obtained vector was transformed with Chaperon Competent Cell BL21 (Takara Bio Inc.) and cultured with shaking in LB medium (500 ml) containing 20 mg/l chloramphenicol, 50 mg/l ampicillin, 10 μl/l tetracycline and 1 g/l L-arabinose for 10 hr at 37° C. When the culture medium showed OD600 of 0.6, 1 mM IPTG was added and the mixture was cultured with shaking at 15° C. for 24 hr.

The grown *E. coli* was recovered by centrifugation, and subjected to protein extraction and Histag purification using QIAexpress Ni-NTA Fast Start Kit (QIAGEN). The purified protein was confirmed by SDS-PAGE. The protein was injected to a rabbit to produce a polyclonal antibody.

Figure 6:
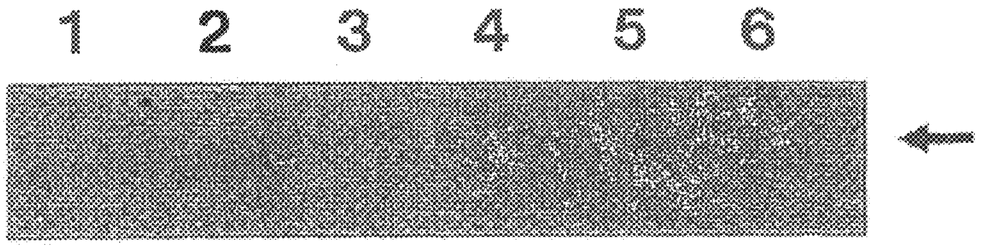
FIG. 6 shows the analysis results of proteins extracted from fruits of transformed chili pepper, by Western blot analysis, wherein each lane is 1: CH-19 Hot, 2: TG-1, 3: TG-3, 4: TG-8, 5: TG-14, 6:CH-19 Sweet.

Using the produced polyclonal antibody, the protein extracted from the fruit was electrophoresed by 1 mg SDS-PAGE and analyzed by Western blot. As a result, TG-3 and TG-8 that showed accumulation of capsiate showed a remarkably decreased pAMT protein amount. Also in TG-14, the pAMT protein amount was lower than CH-19 HOT (FIG. 6).

From the foregoing, it has been shown that suppression of expression of pAMT gene of chili pepper that biosynthesizes capsaicinoids enables production of a plant showing an increased amount of capsinoid biosynthesis.

Example 5

Analysis of Paint Alleles in Three Mildly Pungent Cultivars of Chili Pepper (1) Materials and Methods (a) Plant Material Four *C. chinense* cultivars were used in this study: three mildly pungent cultivars (Zavory Hot, Aji Dulce strain 2, and Belize Sweet), and one pungent cultivar (Red Habanero). All plants were grown at the experimental farm of Kyoto University, from March to October, 2009. The capsinoid and capsaicinoid contents of pepper fruits were determined using HPLC as described below.

(b) Extraction of Capsinoids and Capsaicinoids

To determine the capsinoid and capsaicinoid contents, three immature fruits at approximately 30 days after flowering or mature fruits at approximately 45 days after flowering were used. These fruits become red at the mature fruit stage. Their contents were determined as previously described (*J. Agric. Food Chem.* 2010, 58, 1761-1767). After the pericarps were cut with a knife, whole fruits were dried completely in a freeze drier (FDU-540, EYELA) for 3 days. Dried fruits were ground in a blender (MK-61M, National) at room temperature. A 4-mL volume of acetone (Wako) was added to 200 mg of dry fruit powder. After vortexing, the sample tube was allowed to settle for 15 min at room temperature. The supernatant was collected and 1-mL acetone was added to the residue. Then the supernatant was collected again. After repeating this process, 1-mL ethyl acetate was added to the residue, and the supernatant was collected. The combined supernatant volume was completely evaporated in a rotary evaporator (VC-960, Taitec) at 36° C. under vacuum. The residue was dissolved in 2-mL ethyl acetate, and the resulting solution was filtered into a 2-mL glass vial using a Sep-Pak Cartridge C18 (Waters) and then used for HPLC (Hitachi L-7420 system) analysis.

(c) HPLC Analysis Conditions

The separation was performed on a μ-Bondapak C18 column (10 μm, 3.9 mm×150 mm, Waters) coupled with a guard column (μ-Bondapak Guard-Pak, Waters). The eluent, which was detected at 280 nm with a UV detector, was a mixture of $MeOH/H_2O$ (70:30 v/v) with a flow rate of 1.0 mL/min. The capsinoid content was calculated as the sum of capsiate and dihydrocapsiate and the capsaicinoid content was calculated as that of capsaicin and dihydrocapsaicin.

(d) Genomic Sequence Analysis of p-AMT

Figure 7:
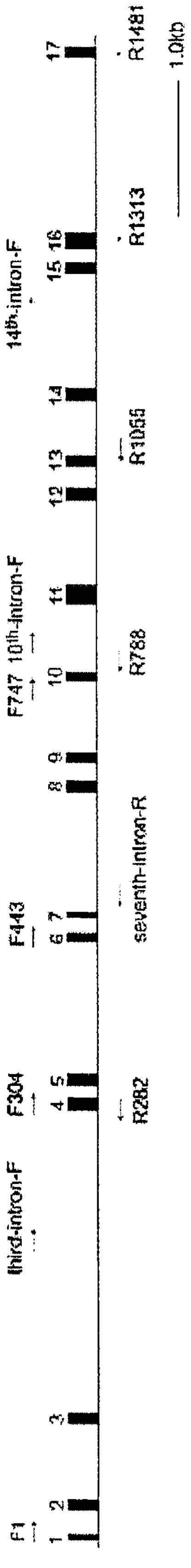
FIG. 7 shows the design and location of primers for genomic PCR of p-AMT gene. Schematic representation of the genomic organization of the p-AMT gene in a pungent cultivar, Red Habanero. Black boxes indicate exons and lines indicate introns. Arrows indicate location of primer. The sequence of each primer is referred to Table 1.

The genomic sequence covering the full-length of p-AMT was determined for pungent and mildly pungent cultivars. Genomic DNA was extracted from young leaves of pepper plants using Nucleon PhytoPure (GE Healthcare, Japan). The p-AMT genomic sequence covering the full-length open reading frame (ORF) was amplified using primer sets: F1 and seventh intron R, F443 and R788, 10th intron F and R1313, F747 and R1055, 14th intron F and R1481 (FIG. 7). The sequences of primers are shown in Table 1.

TABLE 1

Primers used for genomic sequence analysis of p-AMT.

| Primer name | Primer sequence (5′-3′) | SEQ ID NO |
|---|---|---|
| F1 | TCTTTCTCTTTCCTTAGCAAT | (3) |
| third-intron-F | CCCCCTCTTATGGGTGAAAC | (4) |
| R282 | GGCAGCTTCAACAAGTCGAGTC | (5) |
| F304 | GCCATTTTATCATTCATTTTGGA | (6) |
| F443 | GGTGAAGATGGTGTGGTATT | (7) |
| Seventh-intron-R | AAATGATCATGTTATGTTCAAAAA | (8) |
| F747 | TCCTAGGAGCAGCAGGTGTAAT | (9) |
| R788 | AATATGTTGCGGGAGGAAGT | (10) |
| $10^{th}$-intron-F | CCCGCTTTGGTCCTCTCTCTG | (11) |
| R1055 | CAGGGTGTCCGGAATAAGTAAA | (12) |
| $14^{th}$-intron-F | AATATGCTTCGCCCCTAAAT | (13) |
| R1313 | CCAACATCCCGTACTTAGCACA | (14) |
| R1481 | ATAAACAAGCTTTCGCCGTGA | (15) |

The genomic region harboring the insertion in Zavory Hot was amplified using F304 and seventh intron R, and that in Aji Dulce strain 2 was amplified using third intron F and R282. The genomic PCR reaction mixture consisted of 0.5-μL LA Taq polymerase (TAKARA, Japan), 5-μL buffer (provided with the polymerase), 8-μL dNTPs (2 mM), and 1.0-μL forward and reverse primer (20 μM), and was adjusted to 50 μL with super-distilled water. Approximately 30-ng genomic DNA was used as a template. The genomic PCR procedure was as follows: 1 cycle of 2 min at 94° C.; 35 cycles of 10 s at 98° C., 30 s at 55° C. and 15 min at 68° C., with a final extension of 15 min at 68° C. For cloning purposes, the p-AMT sequence amplified by genomic PCR was cloned to a pCR-XL-TOPO® vector using a TOPO® XL PCR Cloning Kit (Invitrogen, Japan). Nucleotide sequencing was carried out in an ABI PRISM 3100 Genetic Analyzer with an ABI PRISM BigDye Terminator v3.1 Cycle Sequencing Kit (Applied Biosystems, Japan).

(e) cDNA Sequence Analysis of p-AMT

The full-length cDNA sequences of p-AMT were determined in pungent and mild pungent cultivars. Pepper fruits were harvested at 30 days after flowering, and the placenta was separated for RNA extraction, because placental dissepiment is the site of capsaicinoid and capsinoid biosynthesis (e.g., *Plant Cell Physiol.* 1980, 21, 839-853). p-AMT is expressed specifically in the placenta (e.g., *Plant J.* 2009, 59, 953-961). Total RNA was extracted from the placenta using a QuickGene RNA Cultured Cell Kit S (Fuji Film, Japan) with some modifications. All RNA used for RT-PCR was treated with DNase I prior to cDNA synthesis to remove DNA contamination. The RT reaction was performed using 0.5 μL ReverTra Ace (TOYOBO, Japan) with a reaction mixture composed of 2-μL RT-buffer, 1-μL dNTPs (10 mM), 0.5-μL RNase Inhibitor, 0.5-μL oligo (dT) primer (20 μM), and 4.5-μL super-distilled water. Total RNA was adjusted to approximately 500 ng/μL and 1 μL was used as a template. This mixture was incubated at 42° C. for 30 min and at 99° C. for 5 min. The full-length cDNA sequence of p-AMT was amplified using primer sets, F1 and R1481. The primer sequences were designed based on the studied nucleotide sequence for p-AMT (GenBank accession number AF085149); they were designed to amplify a 1481 bp fragment of the p-AMT cDNA sequence. The RT-PCR reaction mixture consisted of 1-μL KOD FX polymerase (TOYOBO, Japan), 5-μL buffer (provided with the polymerase), 5-μL dNTPs (2 mM) and 1-μL forward and reverse primer (20 μM) and was adjusted to 50 μL with super distilled water. A 1-μL aliquot of cDNA was used as a template. The PCR procedure to amplify p-AMT was as follows: 1 cycle of 2 min at 96° C.; 35 cycles of 10 s at 98° C., 30 s at 55° C., and 3 min at 68° C.; and a final extension of 10 min at 68° C. RT-PCR products were separated on a 1% agarose gel, stained with ethidium bromide, and visualized using a UV transilluminator. The full-length sequence of p-AMT amplified by RT-PCR was cloned to pUC118 by using a Mighty Cloning Kit (TAKARA, Japan). Nucleotide sequencing was carried out as described above. Blast was applied to analyze nucleotide and derived amino acid sequences as well as multiple alignments.

Figure 8:
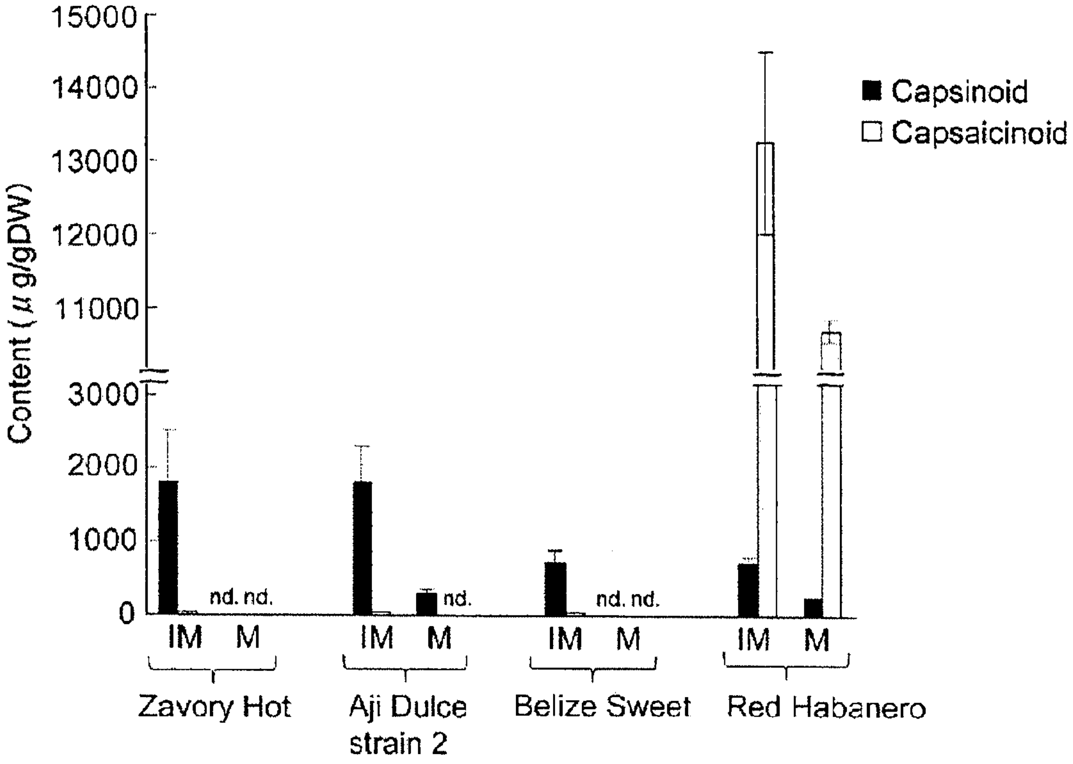
FIG. 8 shows capsinoid and capsaicinoid contents in *C. chinense* cultivars. IM, immature fruit stage; M, mature fruit stage. Bar indicates standard error (n=3).

(2) Results and Discussion (a) Mildly Pungent *C. chinense* Cultivars Contain Capsinoid The pungent cultivar, Red Habanero, mainly contained capsaicinoids and produced capsinoids in trace amounts. On the contrary, the three mildly pungent cultivars contained high levels of capsinoid, and produced capsaicinoid in trace amounts (FIG. 8). The capsinoid content in Zavory Hot, Aji Dulce strain 2, and Belize Sweet was 1812, 1797, and 732 μg/g DW, respectively. Previous studies have shown that the capsinoid content decreased more drastically than capsaicinoid content as fruits matured (*J. Jpn. Soc. Hortic. Sci.* 1989, 58, 601-607*; J. Agric. Food Chem.* 2009, 57, 5407-5412). In mildly pungent cultivars, the capsinoid content also decreased drastically during fruit maturation (FIG. 8). Immature fruit should be collected in order to obtain a high level of capsinoid from these cultivars. Capsinoids, which are esters of a fatty acid and vanillyl alcohol, decompose easily in polar solvents such as water and methanol (*J. Agric. Food Chem.* 2001, 49, 4026-4030). This instability in water could be responsible for its rapid decrease during fruit maturation.

(b) Genomic Sequence Analysis of p-AMT Alleles

Figure 9A:
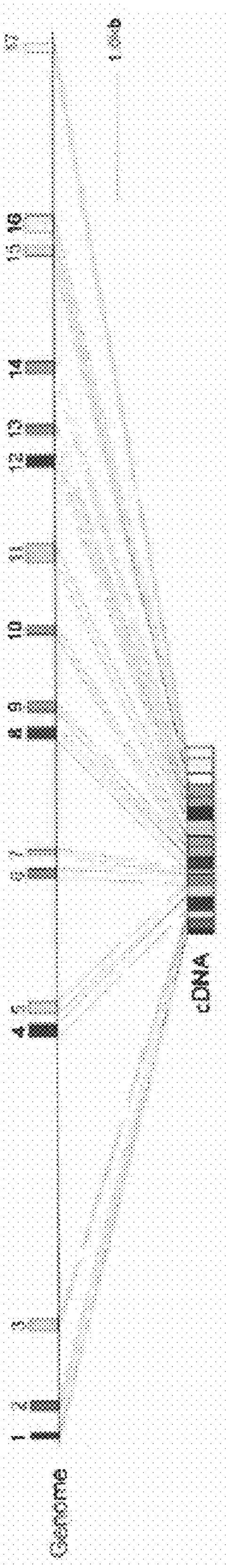
FIG. 9 shows schematic diagrams of the p-amt allele and RT-PCR-derived cDNAs in *C. chinense* cultivars. (A) Schematic representation of the genomic organization of the p-AMT gene in a pungent cultivar, Red Habanero. Colored boxes indicate exons and lines indicate introns. The cDNA encodes a full-length open reading frame of p-AMT. The three mildly pungent cultivars have loss-of-function p-amt alleles, which contain a transposable element of *C. chinense* (Tcc) or a short nucleotides insertion. (B) Schematic representation of the p-amt$^{Belize\ Sweet}$ allele and cDNA sequence. The p-amt$^{Belize\ Sweet}$ allele contains a 5 bp insertion (TGGGC) in the eighth exon, which leads to a frameshift mutation. (C) Schematic representation of the p-amt$^{Zavory\ Hot}$ allele and cDNA sequence. The p-amt$^{Zavory\ Hot}$ allele contains Tcc in the fifth intron region. Tcc is a member of the hAT transposon superfamily and is 2.3 kb long. The cDNAs in Zavory Hot have insertions of the Tcc sequence between the fifth and sixth exons. Splice variants were identified by sequencing cDNA fragments, none of which encodes the full-length p-AMT open reading frame. (D) Schematic representation of the p-amt$^{Aji\ Dulce\ strain\ 2}$ allele and cDNA sequences. The p-amt$^{Aji\ Dulce\ strain\ 2}$ allele contains Tcc in the third intron region. The cDNAs in Aji Dulce strain 2 also have insertions of the Tcc sequence between the third and fourth exons. In addition, some cDNAs contain second intron sequences, and 8 bp insertion (GCCACACC) in the sixth exon.
Figure 9B:
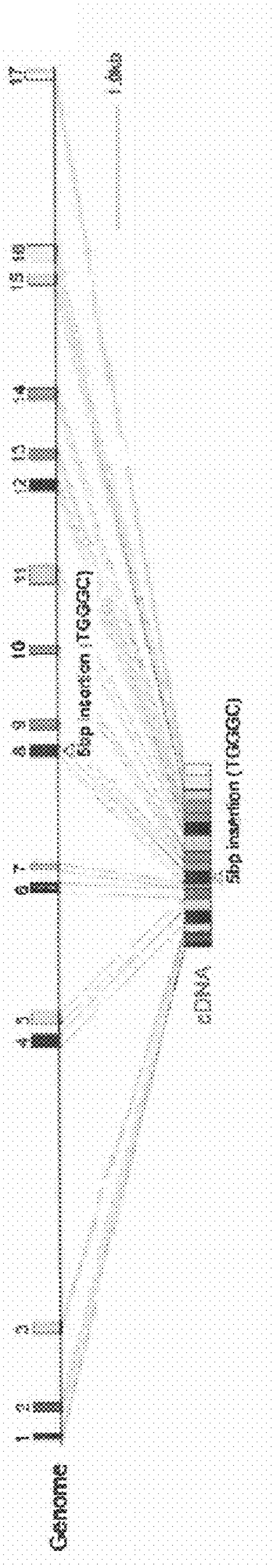
Figure 9C:
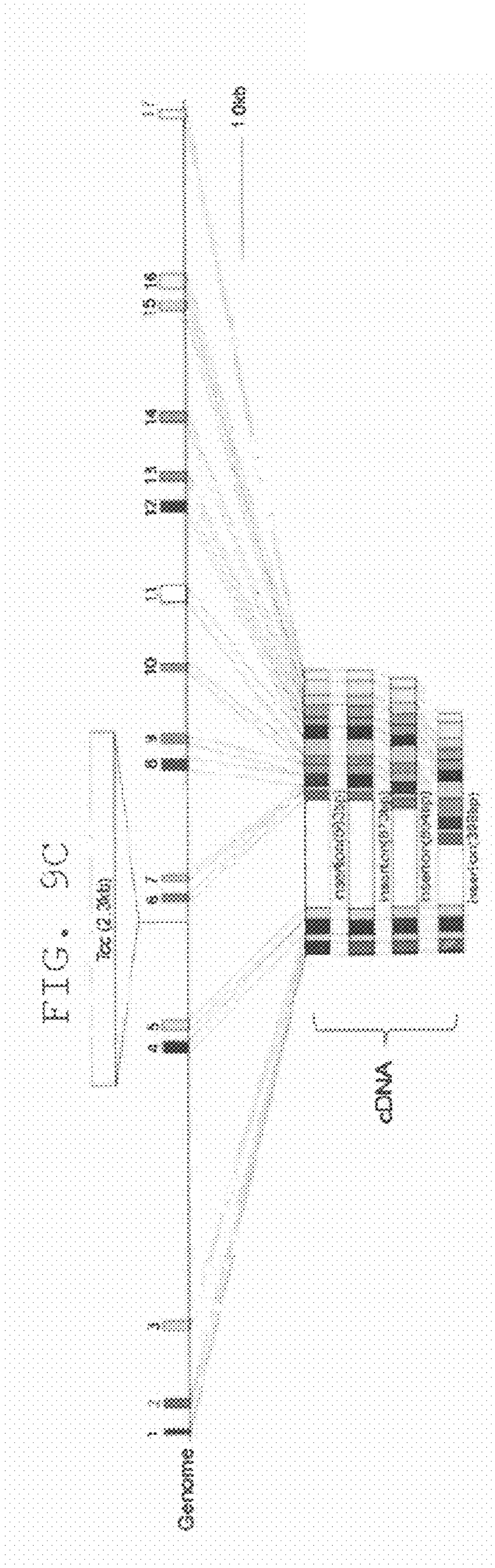
Figure 10:
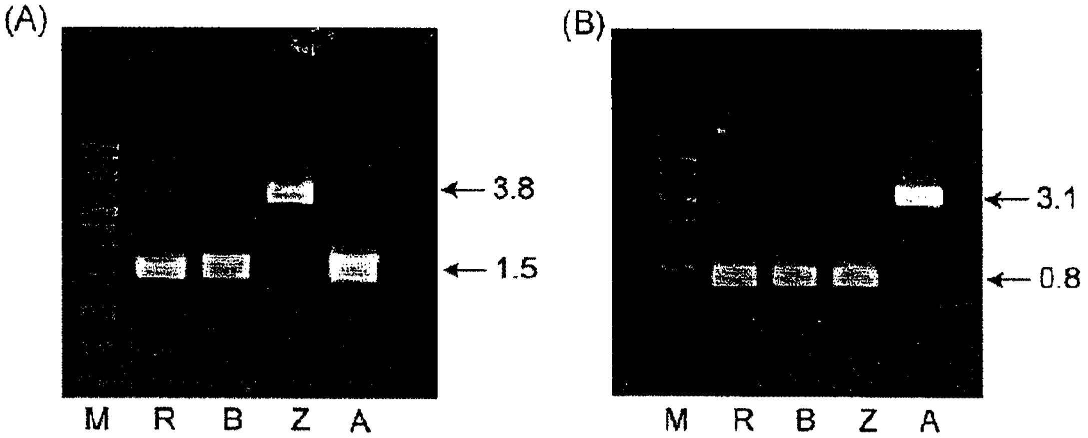
FIG. 10 shows genomic PCR analysis of p-AMT. M, DNA ladder marker; R, Red Habanero; B, Belize Sweet; Z, Zavory Hot; A, Aji Dulce strain 2. (A) Amplification of the region between the fourth exon and seventh intron. Primer F304 and seventh-intron-R were used. (B) Amplification of the region between the third intron and fourth exon. Primer third-intron-F and R282 were used. The size of the amplified fragment is indicated to the left (kb).

Next, the p-AMT gene was investigated to identify the genetic mechanism of capsinoid biosynthesis in mildly pungent *C. chinense* cultivars. The p-AMT genomic sequence corresponding to the ORF was amplified from the pungent cultivar, Red Habanero, and the resulting 11 kb sequence was determined. The p-AMT of Red Habanero consists of 17 exons separated by 16 introns and its sequence is very similar to that of the *C. annuum* cultivars (FIG. 9A). The p-AMT of Belize Sweet also consists of 17 exons, but a 5 bp insertion (TGGGC) was found in the eighth exon (FIG. 9B). In Zavory Hot and Aji Dulce strain 2, insertions of transposable elements were found in introns of p-AMT (FIG. 9C, D). When a genomic region between the fourth exon and seventh intron was amplified, a 1.5 kb fragment was obtained from the *C. chinense* cultivars except for Zavory Hot (FIG. 10A). In contrast, a 3.8 kb fragment from Zavory Hot was amplified, cloned, and sequenced. A distinct long insertion sequence was found in this fragment. The insertion sequence was 2299 bp long and was located in the 3' part of the fifth intron (FIG. 9C). A short open reading frame (104 amino acids in length) was found in this insertion sequence and showed similarity in its amino acid sequence to the hAT dimerization domain. This insertion sequence contained 23 bp terminal inverted repeats with an 8 bp target site duplication (CCCTTACA). These structure characteristics indicated that this insertion is a member of the hAT transposon superfamily. We named this element, a "Transposon of *C. chinense*" (Tcc). Tcc appears to be nonautonomous because it is not long enough for its amino acid sequence to encode the entire transposase. When a genomic region between the third intron and the fourth exon was amplified, a 0.8 kb fragment was obtained from the *C. chinense* cultivars except Aji Dulce strain 2 (FIG. 10B). In contrast, a 3.1 kb fragment from Aji Dulce strain 2 was amplified, cloned, and sequenced. This insertion is identical to Tcc with an 8 bp target site duplication (CTATGACC). In addition, an 8 bp insertion (GCCACACC) was found in the sixth exon of Aji Dulce strain 2 (FIG. 10D).

(c) Aberrant p-AMT mRNAs are Expressed in Mildly Pungent Cultivars

Figure 11:
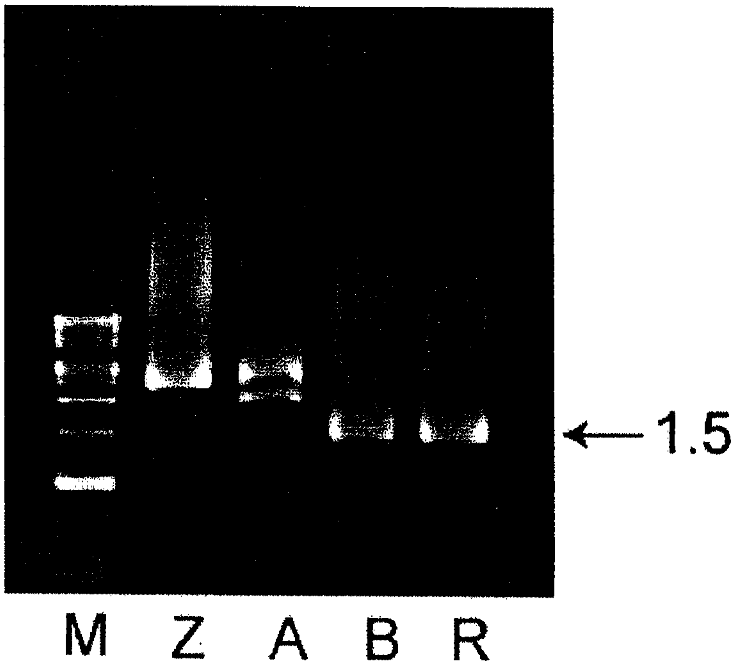
FIG. 11 shows RT-PCR for full length of p-AMT in *C. chinense* cultivars. Z, Zavory Hot; A, Aji Dulce strain 2; B, Belize Sweet; R, Red Habanero. Zavory Hot, Aji Dulce Strain 2 and Belize Sweet are mildly pungent cultivars containing capsinoid. Red Habanero is a pungent cultivar. Primers for RT-PCR were designed to amplify the full-length coding sequence of p-AMT (1481 bp). The size of the amplified fragment is indicated to the left (kb).

Analysis of the p-AMT expression by RT-PCR was conducted with a primer set of F1 and R1481. The 1.5 kb fragments were amplified in Red Habanero and Belize Sweet, but larger cDNA fragments were amplified in Zavory Hot and Aji Dulce strain 2 (FIG. 11). cDNA sequences of p-AMT were determined in these cultivars. FIG. 9 shows a schematic representation of the genomic sequence of p-AMT, and a graphic summary of distinct RT-PCR cDNA clones derived from the placenta. In Red Habanero, all cDNA sequences contained a complete ORF of 1377 by encoding a putative aminotransferase of 459 amino acids (FIG. 9A). p-AMT of Red Habanero is completely identical to that of a pungent cultivar (GenBank accession number AF085149) in the amino acid sequence. This result indicates that mRNAs encoding functional p-AMT are synthesized in the placenta of Red Habanero.

Figure 9D:
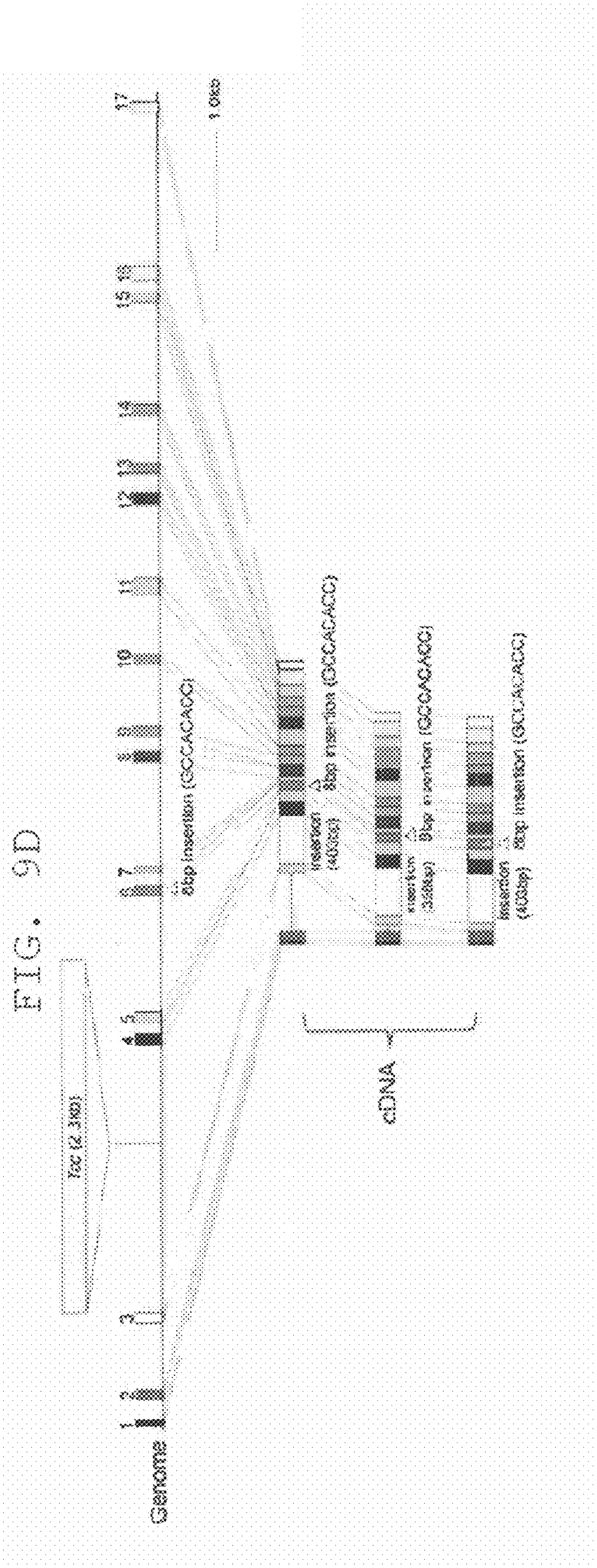

In contrast, cDNA sequences encoding p-AMT were not detected in mildly pungent cultivars. The p-AMT cDNA of Belize Sweet contains a 5 bp insertion at the eighth exon, which results in a frameshift mutation (FIG. 9B). This would lead to a truncated protein of 217 amino acids lacking the PLP-binding domain, which is an important domain for aminotransferase activity and is present in the p-AMT of pungent cultivars. Therefore, the insertion at the eighth exon could prevent the translation of the active p-AMT in Belize Sweet. The p-AMT cDNAs of Zavory Hot contained a 400-900 bp insertion between the fifth and sixth exons (FIG. 9C). The sequence of the insertion is identical to a part of Tcc. The insertion position corresponds to that of Tcc in the genomic sequence. The p-AMT cDNAs of Aji Dulce strain 2 also contain a part of the Tcc sequence between the third and fourth exons (FIG. 9D). In addition, an 8 bp nucleotide (GCCACACC) and second intron sequence were inserted into the cDNA of the Aji Dulce strain 2. Tcc insertions in the p-AMT cDNA sequence could lead to a frameshift mutation, resulting in a truncated p-AMT. It has been shown that the insertion of a transposable element changes the splicing pattern of a gene, resulting in an mRNA containing a sequence of the element (*Plant Cell Physiol.* 2003, 44, 990-1001). The Tcc insertion at the intron region could change the splicing pattern of p-AMT gene, and the mRNA containing the Tcc sequence and some splice variants could be synthesized.

p-AMT cDNA sequence analysis suggests that functional p-AMT mRNAs were not produced in mildly pungent cultivars. Taken together with the genomic sequences, mildly pungent cultivars have loss-of-function alleles of p-amt, designated as p-amt$^{Belize\ Sweet}$, p-amt$^{Zavory\ Hot}$, and p-amt$^{Aji\ Dulce\ strain\ 2}$. A loss-of-function p-amt allele could suppress the formation of vanillylamine from vanillin, producing vanillyl alcohol instead, which in turn result in capsinoid formation in mildly pungent cultivars, such as in CH-19 Sweet and Himo (FIG. 1).

Here it was revealed that the three mildly pungent cultivars have novel loss-of-function alleles of p-amt. These p-amt alleles have a transposon (Tcc) or short inserted nucleotides (FIG. 9). The inserted positions are different among the three cultivars, suggesting that these mutations occurred independently in the breeding process of the *C. chinense* cultivars. Therefore, mildly pungent *C. chinense* cultivars were generated not by single mutation but multiple loss-of-function mutations in p-amt.

Two out of three p-amt alleles are generated by Tcc insertion. Tcc insertion was not found in p-amt$^{Belize\ Sweet}$, but this allele has a 5 bp insertion (TGGGC) in the eighth exon. It has been found that the excision of the hAT family transposon from a given site can generate 5-8 bp nucleotides, called footprints (*Plant Cell Physiol.* 2006, 47, 1473-1483). These extra sequences can cause a frameshift mutation. The 5 bp insertion (TGGGC) in the p-amt$^{Belize\ Sweet}$ allele could be a footprint generated by insertion and the subsequent excision of a transposon, such as Tcc. It was assumed that Tcc could widely contribute to the generations of mild pungency in *C. chinense.*

INDUSTRIAL APPLICABILITY

According to the present invention, capsinoids can be highly produced from a plant conventionally incapable of producing capsinoids or capable of producing capsinoids in a low amount. The present invention is useful since it can provide capsinoids, which are expected to be applicable to various fields such as medicines, health foods and the like, in large amounts at a low cost.

The invention claimed is:

1. A method of producing a genetically modified plant having an increased capability to produce capsinoids, comprising:

(a) introducing a DNA encoding an antisense RNA against putative aminotransferase (pAMT) mRNA into a plant that is a pungent variety belonging to the genus *Capsicum* and produces capsaicinoids in its fruit to produce a genetically modified plant, wherein the antisense RNA against pAMT mRNA is complementary to an mRNA of the endogenous pAMT gene of the plant, and has a nucleotide sequence having 95% or more identity to the nucleotide sequence of SEQ ID NO:1 from *Capsicum annuum* CH-19 Hot, (b) measuring the content of capsinoids in a fruit of the genetically modified plant from (a), and (c) selecting the genetically modified plant from (b) having an increased amount of capsinoids production as compared to that of the corresponding non-genetically modified plant.

2. The method of claim 1, further comprising recovering a capsinoid from said genetically modified plant.

3. A method of producing capsinoid, comprising recovering the capsinoid from a fruit of a plant obtained by the method according to claim 1.

4. The method of claim 1, wherein the plant that is a pungent variety belonging to the genus *Capsicum* is *C. annuum, C. baccatum, C. chinense, C. frutescens* or *C. pubescens.*

5. The method of claim 1, wherein the plant that is a pungent variety belonging to the genus *Capsicum* is *C. annuum* variety 'Takanotsume', CH-19 Hot, Yatsufusa', 'Toranoo' or 'Fushimiama'.

6. The method of claim 1, wherein the plant that is a pungent variety belonging to the genus *Capsicum* is *C. baccatum* aji amarillo.

7. The method of claim 1, wherein the plant that is a pungent variety belonging to the genus *Capsicum* is *C. chinense* habanero pepper or Bhut Jolokia.

8. The method of claim 1, wherein the plant that is a pungent variety belonging to the genus *Capsicum* is *C. frutescens.*

9. The method of claim 1, wherein the plant that is a pungent variety belonging to the genus *Capsicum* is *C. pubescens* rocoto.

10. The method of claim 1, wherein the plant that is a pungent variety belonging to the genus *Capsicum* is *C. chinese* Zavory hot, Aji Dulce strain 2, Belize sweet or Red Habanero.

11. The method of claim 1, wherein the antisense RNA against pAMT mRNA has the nucleotide sequence having 97% or more identity to the nucleotide sequence of SEQ ID NO:1 from *Capsicum annuum* CH-19 Hot.

12. The method of claim 1, wherein the antisense RNA against pAMT mRNA has the nucleotide sequence of the pAMT gene from *Capsicum annuum* CH-19 Sweet.

* * * * *

SEQUENCE LISTING

```
<160> NUMBER OF SEQ ID NOS: 15

<210> SEQ ID NO 1
<211> LENGTH: 1616
<212> TYPE: DNA
<213> ORGANISM: Capsicum annuum (variety CH-19 hot)
<220> FEATURE:
<221> NAME/KEY: CDS
<222> LOCATION: (77)..(1456)

<400> SEQUENCE: 1

tctttctctt tccttagcaa ttttctccat attttgacta attattaagt cataattttc      60

aagaaatctt gaagga atg gcc aat att act aat gaa ttt atg gga cat gat     112
                  Met Ala Asn Ile Thr Asn Glu Phe Met Gly His Asp
                  1               5                   10

atg ttg gca ccc ttt act gcg gga tgg cag agt gat atg gaa cct tta      160
Met Leu Ala Pro Phe Thr Ala Gly Trp Gln Ser Asp Met Glu Pro Leu
        15                  20                  25

gtt ata gaa aag tcg gag ggc tct tat gtc tat gac ata aat ggg aag      208
Val Ile Glu Lys Ser Glu Gly Ser Tyr Val Tyr Asp Ile Asn Gly Lys
    30                  35                  40

aag tat ctt gac act tta tct ggt tta tgg tgc aca aca tta ggg gga      256
Lys Tyr Leu Asp Thr Leu Ser Gly Leu Trp Cys Thr Thr Leu Gly Gly
45                  50                  55                  60

agt gag act cga ctt gtt gaa gct gca aat aaa caa ctc aat aca ttg      304
Ser Glu Thr Arg Leu Val Glu Ala Ala Asn Lys Gln Leu Asn Thr Leu
                65                  70                  75

cca ttt tat cat tca ttt tgg aat cga acc aca aaa cct tct ttg gat      352
Pro Phe Tyr His Ser Phe Trp Asn Arg Thr Thr Lys Pro Ser Leu Asp
            80                  85                  90

ctt gca aag gag ctc cta aat atg ttt act gca aat aaa atg gcc aaa      400
Leu Ala Lys Glu Leu Leu Asn Met Phe Thr Ala Asn Lys Met Ala Lys
        95                  100                 105

gtt ttt ttc act aat agc gga tca gaa gcc aat gac act cag gtg aag      448
Val Phe Phe Thr Asn Ser Gly Ser Glu Ala Asn Asp Thr Gln Val Lys
    110                 115                 120

ctg gtg tgg tat tac aat aat gcc ctt ggg agg cca cag aaa aag aaa      496
Leu Val Trp Tyr Tyr Asn Asn Ala Leu Gly Arg Pro Gln Lys Lys Lys
125                 130                 135                 140

att att gct cga gca aaa gca tat cat ggt tcc act tac att tct gct      544
Ile Ile Ala Arg Ala Lys Ala Tyr His Gly Ser Thr Tyr Ile Ser Ala
                145                 150                 155

ggt ctc tct ggg ctt cct cca atg cat caa aaa ttt gat ttg cca cct      592
Gly Leu Ser Gly Leu Pro Pro Met His Gln Lys Phe Asp Leu Pro Pro
            160                 165                 170

cca ttt gtt ctg cac act gag tgc cct cat tat tgg gcc tat cac ttg      640
```

-continued

```
Pro Phe Val Leu His Thr Glu Cys Pro His Tyr Trp Ala Tyr His Leu
        175                 180                 185

cca ggt gaa acc gaa gag gaa ttc tct act agg ttg gca aat aat ttg      688
Pro Gly Glu Thr Glu Glu Glu Phe Ser Thr Arg Leu Ala Asn Asn Leu
    190                 195                 200

gaa agt ctt ata ctc aac gag ggg cct gaa aca gta gct gct ttc att      736
Glu Ser Leu Ile Leu Asn Glu Gly Pro Glu Thr Val Ala Ala Phe Ile
205                 210                 215                 220

gcc gaa cca gtc cta gga gca gca ggt gta ata ctt cct ccc gca aca      784
Ala Glu Pro Val Leu Gly Ala Ala Gly Val Ile Leu Pro Pro Ala Thr
                225                 230                 235

tat ttt gat aag gtt caa gct att tta agg aaa cat gac att ctt ttt      832
Tyr Phe Asp Lys Val Gln Ala Ile Leu Arg Lys His Asp Ile Leu Phe
            240                 245                 250

atc gcg gat gag gtg gta tgt gga ttt gga aga ctt ggg aca atg ttt      880
Ile Ala Asp Glu Val Val Cys Gly Phe Gly Arg Leu Gly Thr Met Phe
        255                 260                 265

ggc agt gat aaa tac aac att aaa cct gat ctt gtc tct gta gca aag      928
Gly Ser Asp Lys Tyr Asn Ile Lys Pro Asp Leu Val Ser Val Ala Lys
    270                 275                 280

gca ctt tct tct gga tat atg cca att gcc gct gtc ctt gta agc cag      976
Ala Leu Ser Ser Gly Tyr Met Pro Ile Ala Ala Val Leu Val Ser Gln
285                 290                 295                 300

aaa att tct agt gtc atc ctt tct gaa agc aat aaa att ggt gcc ttt     1024
Lys Ile Ser Ser Val Ile Leu Ser Glu Ser Asn Lys Ile Gly Ala Phe
                305                 310                 315

tgc cat gga ttt act tat tcc gga cac cct gtt gcg tgc gca gtt gca     1072
Cys His Gly Phe Thr Tyr Ser Gly His Pro Val Ala Cys Ala Val Ala
            320                 325                 330

ttg gaa gca ttg aag atc tat aag gaa aga aat att act gag gtg gtg     1120
Leu Glu Ala Leu Lys Ile Tyr Lys Glu Arg Asn Ile Thr Glu Val Val
        335                 340                 345

aac aaa ata tca caa aag ttt caa gaa ggt ttg aaa gca ttc gcc gac     1168
Asn Lys Ile Ser Gln Lys Phe Gln Glu Gly Leu Lys Ala Phe Ala Asp
    350                 355                 360

agt ccc ata att ggg gag ata agg gga act ggt ttg gca ctt tct aca     1216
Ser Pro Ile Ile Gly Glu Ile Arg Gly Thr Gly Leu Ala Leu Ser Thr
365                 370                 375                 380

gag ttt gtg aac aat aaa tct cct aat gat ccc ttt cca tat gaa tgg     1264
Glu Phe Val Asn Asn Lys Ser Pro Asn Asp Pro Phe Pro Tyr Glu Trp
                385                 390                 395

gct gtc ggt aca tat ttt gga gca caa tgt gct aag tac ggg atg ttg     1312
Ala Val Gly Thr Tyr Phe Gly Ala Gln Cys Ala Lys Tyr Gly Met Leu
            400                 405                 410

gta agt tcc act ggt gat cat gta aat atg gct cca cca ttt acc ttg     1360
Val Ser Ser Thr Gly Asp His Val Asn Met Ala Pro Pro Phe Thr Leu
        415                 420                 425

agt ctt gaa gaa ctt gat gag ttg ata cgc ata tat ggg aaa gca ttg     1408
Ser Leu Glu Glu Leu Asp Glu Leu Ile Arg Ile Tyr Gly Lys Ala Leu
    430                 435                 440

aag gat act gaa aag aga gtt gaa gaa ctc aag tct cag aag aag taa     1456
Lys Asp Thr Glu Lys Arg Val Glu Glu Leu Lys Ser Gln Lys Lys
445                 450                 455

aagctcacgg cgaaagcttg tttatcctaa aaaagaagag agaaaaaatg atcagatttc   1516

ctctttgtgc tattctacta gtaataaata atgttctcct tgcaactttg cactagagat   1576

tttctattga aagagctttt gttatccaca attatttaca                         1616


<210> SEQ ID NO 2
```

-continued

```
<211> LENGTH: 459
<212> TYPE: PRT
<213> ORGANISM: Capsicum annuum (variety CH-19 hot)

<400> SEQUENCE: 2

Met Ala Asn Ile Thr Asn Glu Phe Met Gly His Asp Met Leu Ala Pro
1               5                   10                  15

Phe Thr Ala Gly Trp Gln Ser Asp Met Glu Pro Leu Val Ile Glu Lys
            20                  25                  30

Ser Glu Gly Ser Tyr Val Tyr Asp Ile Asn Gly Lys Lys Tyr Leu Asp
        35                  40                  45

Thr Leu Ser Gly Leu Trp Cys Thr Thr Leu Gly Gly Ser Glu Thr Arg
    50                  55                  60

Leu Val Glu Ala Ala Asn Lys Gln Leu Asn Thr Leu Pro Phe Tyr His
65                  70                  75                  80

Ser Phe Trp Asn Arg Thr Thr Lys Pro Ser Leu Asp Leu Ala Lys Glu
                85                  90                  95

Leu Leu Asn Met Phe Thr Ala Asn Lys Met Ala Lys Val Phe Phe Thr
            100                 105                 110

Asn Ser Gly Ser Glu Ala Asn Asp Thr Gln Val Lys Leu Val Trp Tyr
        115                 120                 125

Tyr Asn Asn Ala Leu Gly Arg Pro Gln Lys Lys Lys Ile Ile Ala Arg
    130                 135                 140

Ala Lys Ala Tyr His Gly Ser Thr Tyr Ile Ser Ala Gly Leu Ser Gly
145                 150                 155                 160

Leu Pro Pro Met His Gln Lys Phe Asp Leu Pro Pro Pro Phe Val Leu
                165                 170                 175

His Thr Glu Cys Pro His Tyr Trp Ala Tyr His Leu Pro Gly Glu Thr
            180                 185                 190

Glu Glu Glu Phe Ser Thr Arg Leu Ala Asn Asn Leu Glu Ser Leu Ile
        195                 200                 205

Leu Asn Glu Gly Pro Glu Thr Val Ala Ala Phe Ile Ala Glu Pro Val
    210                 215                 220

Leu Gly Ala Ala Gly Val Ile Leu Pro Pro Ala Thr Tyr Phe Asp Lys
225                 230                 235                 240

Val Gln Ala Ile Leu Arg Lys His Asp Ile Leu Phe Ile Ala Asp Glu
                245                 250                 255

Val Val Cys Gly Phe Gly Arg Leu Gly Thr Met Phe Gly Ser Asp Lys
            260                 265                 270

Tyr Asn Ile Lys Pro Asp Leu Val Ser Val Ala Lys Ala Leu Ser Ser
        275                 280                 285

Gly Tyr Met Pro Ile Ala Ala Val Leu Val Ser Gln Lys Ile Ser Ser
    290                 295                 300

Val Ile Leu Ser Glu Ser Asn Lys Ile Gly Ala Phe Cys His Gly Phe
305                 310                 315                 320

Thr Tyr Ser Gly His Pro Val Ala Cys Ala Val Ala Leu Glu Ala Leu
                325                 330                 335

Lys Ile Tyr Lys Glu Arg Asn Ile Thr Glu Val Val Asn Lys Ile Ser
            340                 345                 350

Gln Lys Phe Gln Glu Gly Leu Lys Ala Phe Ala Asp Ser Pro Ile Ile
        355                 360                 365

Gly Glu Ile Arg Gly Thr Gly Leu Ala Leu Ser Thr Glu Phe Val Asn
    370                 375                 380

Asn Lys Ser Pro Asn Asp Pro Phe Pro Tyr Glu Trp Ala Val Gly Thr
```

-continued

```
385                 390                 395                 400

Tyr Phe Gly Ala Gln Cys Ala Lys Tyr Gly Met Leu Val Ser Ser Thr
                405                 410                 415

Gly Asp His Val Asn Met Ala Pro Pro Phe Thr Leu Ser Leu Glu Glu
            420                 425                 430

Leu Asp Glu Leu Ile Arg Ile Tyr Gly Lys Ala Leu Lys Asp Thr Glu
        435                 440                 445

Lys Arg Val Glu Glu Leu Lys Ser Gln Lys Lys
    450                 455


<210> SEQ ID NO 3
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 3

tctttctctt tccttagcaa t                                              21


<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4

ccccctctta tgggtgaaac                                                20


<210> SEQ ID NO 5
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 5

ggcagcttca acaagtcgag tc                                             22


<210> SEQ ID NO 6
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 6

gccattttat cattcatttt gga                                            23


<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7

ggtgaagatg gtgtggtatt                                                20


<210> SEQ ID NO 8
<211> LENGTH: 24
<212> TYPE: DNA
<213> ORGANISM: Artificial Sequence
```

-continued

<220> FEATURE:
<223> OTHER INFORMATION: Synthetic Oligonucleotide

<400> SEQUENCE: 8
aaatgatcat gttatgttca aaaa 24

<210> SEQ ID NO 9
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 9
tcctaggagc agcaggtgta at 22

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 10
aatatgttgc gggaggaagt 20

<210> SEQ ID NO 11
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 11
cccgctttgg tcctctctct g 21

<210> SEQ ID NO 12
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 12
cagggtgtcc ggaataagta aa 22

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 13
aatatgcttc gcccctaaat 20

<210> SEQ ID NO 14
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 14
ccaacatccc gtacttagca ca 22

-continued

```
<210> SEQ ID NO 15
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 15

ataaacaagc tttcgccgtg a                                              21
```